(12) United States Patent
Ibranyan et al.

(10) Patent No.: US 8,434,528 B2
(45) Date of Patent: May 7, 2013

(54) SYSTEMS AND METHODS FOR RESERVOIR FILLING

(75) Inventors: Arsen Ibranyan, Glendale, CA (US); Julian D. Kavazov, Arcadia, CA (US); David Hezzell, Thousand Oaks, CA (US); Christopher G. Griffin, Sylmar, CA (US); Benjamin X. Shen, Davis, CA (US); Mike Lee, Glendale, CA (US); Thomas Miller, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1408 days.

(21) Appl. No.: 12/111,751

(22) Filed: Apr. 29, 2008

(65) Prior Publication Data

US 2008/0269680 A1 Oct. 30, 2008

Related U.S. Application Data

(60) Provisional application No. 60/927,032, filed on Apr. 30, 2007.

(51) Int. Cl.
*B65B 1/04* (2006.01)
(52) U.S. Cl.
USPC .............. 141/18; 141/2; 141/329; 222/386.5; 222/394
(58) Field of Classification Search .................. 222/394, 222/386, 386.5; 141/2, 18, 23, 24, 25, 285, 141/329, 330
See application file for complete search history.

(56) References Cited

U.S. PATENT DOCUMENTS

| | | | |
|---|---|---|---|
| 1,948,982 A | | 2/1934 | Cutter |
| 2,064,815 A | | 12/1936 | Armstrong |
| 2,570,625 A | | 10/1951 | Zimmerman et al. |
| 2,644,450 A | | 7/1953 | Krewson |
| RE24,918 E | * | 1/1961 | Mills ........................... 222/386.5 |
| 2,973,758 A | | 3/1961 | Murrish |
| 3,223,289 A | * | 12/1965 | Bouet ........................... 222/209 |
| 3,342,180 A | | 9/1967 | Sandhage |
| 3,343,422 A | * | 9/1967 | McSmith .................... 73/864.03 |
| 3,572,552 A | * | 3/1971 | Guinn ........................... 222/263 |
| 3,623,474 A | | 11/1971 | Heilman et al. |
| 3,650,093 A | * | 3/1972 | Rosenberg ........................... 96/6 |
| 3,662,753 A | | 5/1972 | Tassell |

(Continued)

FOREIGN PATENT DOCUMENTS

| | | |
|---|---|---|
| DE | 10 2004 055 870 A | 5/2006 |
| DE | 20 2007 006 363 U1 | 8/2007 |

(Continued)

OTHER PUBLICATIONS

Office Action dated Dec. 22, 2010 from related U.S. Appl. No. 12/111,815.

(Continued)

*Primary Examiner* — Jason K Niesz
(74) *Attorney, Agent, or Firm* — Foley & Lardner LLP

(57) ABSTRACT

Systems and methods allow for limiting a presence of air bubbles in a fluidic medium filled into a reservoir. A fluidic medium may be forced from a vial into a reservoir. A vial may be degassed prior to being used to fill a reservoir. A filling process may be automated and a membrane may be located in a fluid flow path to trap air bubbles in a fluidic medium being filled into a reservoir.

14 Claims, 31 Drawing Sheets

U.S. PATENT DOCUMENTS

| | | | |
|---|---|---|---|
| 3,729,032 A * | 4/1973 | Tischlinger et al. | 141/2 |
| 3,802,430 A | 4/1974 | Schwebel et al. | |
| 3,963,151 A | 6/1976 | North, Jr. | |
| 3,993,061 A | 11/1976 | O'Leary | |
| 4,064,879 A | 12/1977 | Leibinsohn | |
| 4,089,624 A | 5/1978 | Nichols et al. | |
| 4,117,841 A | 10/1978 | Perrotta et al. | |
| 4,215,701 A | 8/1980 | Raitto | |
| 4,219,055 A | 8/1980 | Wright | |
| 4,234,108 A * | 11/1980 | Diamond | 222/386 |
| 4,373,535 A | 2/1983 | Martell | |
| 4,392,850 A | 7/1983 | Elias et al. | |
| 4,434,820 A | 3/1984 | Glass | |
| 4,448,206 A | 5/1984 | Martell | |
| 4,493,704 A | 1/1985 | Beard et al. | |
| 4,568,336 A | 2/1986 | Cooper | |
| 4,572,210 A | 2/1986 | McKinnon | |
| 4,585,435 A * | 4/1986 | Vaillancourt | 604/518 |
| 4,684,365 A | 8/1987 | Reinicke | |
| 4,684,366 A | 8/1987 | Denny et al. | |
| 4,703,763 A | 11/1987 | McAlister et al. | |
| 4,743,249 A | 5/1988 | Loveland | |
| 4,744,955 A | 5/1988 | Shapiro | |
| 4,759,756 A | 7/1988 | Forman et al. | |
| 4,838,857 A | 6/1989 | Strowe et al. | |
| 4,865,592 A | 9/1989 | Rycroft | |
| 4,883,101 A | 11/1989 | Strong | |
| 4,913,703 A | 4/1990 | Pasqualucci et al. | |
| 4,957,637 A | 9/1990 | Cornell | |
| 4,976,696 A | 12/1990 | Sanderson et al. | |
| 4,986,820 A | 1/1991 | Fischer | |
| 4,994,034 A | 2/1991 | Botich et al. | |
| 5,002,527 A | 3/1991 | Reller et al. | |
| 5,045,096 A * | 9/1991 | Quang et al. | 96/155 |
| 5,049,129 A | 9/1991 | Zdeb et al. | |
| 5,053,001 A | 10/1991 | Reller et al. | |
| 5,062,834 A | 11/1991 | Gross et al. | |
| 5,090,963 A | 2/1992 | Gross et al. | |
| 5,115,948 A * | 5/1992 | Johnson | 222/209 |
| 5,156,591 A | 10/1992 | Gross et al. | |
| 5,176,502 A | 1/1993 | Sanderson et al. | |
| 5,186,805 A | 2/1993 | Gross et al. | |
| 5,190,522 A | 3/1993 | Wojcicki et al. | |
| 5,203,506 A | 4/1993 | Gross et al. | |
| 5,232,449 A | 8/1993 | Stern et al. | |
| 5,242,406 A | 9/1993 | Gross et al. | |
| 5,242,408 A | 9/1993 | Jhuboo et al. | |
| 5,246,147 A | 9/1993 | Gross | |
| 5,254,096 A | 10/1993 | Rondelet et al. | |
| 5,259,732 A | 11/1993 | Stern | |
| 5,261,884 A | 11/1993 | Stern et al. | |
| 5,275,582 A | 1/1994 | Wimmer | |
| 5,284,570 A | 2/1994 | Savage et al. | |
| 5,292,318 A | 3/1994 | Haber et al. | |
| 5,295,966 A | 3/1994 | Stern et al. | |
| 5,295,967 A | 3/1994 | Rondelet et al. | |
| 5,308,333 A * | 5/1994 | Skakoon | 604/110 |
| 5,312,364 A | 5/1994 | Jacobs | |
| 5,356,632 A | 10/1994 | Gross et al. | |
| 5,367,891 A | 11/1994 | Furuyama | |
| 5,385,559 A | 1/1995 | Mannix | |
| 5,387,450 A | 2/1995 | Stewart | |
| 5,407,434 A | 4/1995 | Gross | |
| 5,409,236 A | 4/1995 | Therrien | |
| 5,425,706 A | 6/1995 | Gross et al. | |
| 5,496,285 A | 3/1996 | Schumacher et al. | |
| 5,527,288 A | 6/1996 | Gross et al. | |
| 5,533,964 A | 7/1996 | Halperin et al. | |
| 5,697,916 A | 12/1997 | Schraga | |
| 5,704,520 A | 1/1998 | Gross | |
| 5,800,420 A | 9/1998 | Gross et al. | |
| 5,807,375 A | 9/1998 | Gross et al. | |
| 5,820,622 A | 10/1998 | Gross et al. | |
| 5,848,991 A | 12/1998 | Gross et al. | |
| 5,851,549 A | 12/1998 | Svec | |
| 5,858,001 A | 1/1999 | Tsals et al. | |
| 5,865,803 A | 2/1999 | Major | |
| 5,871,125 A | 2/1999 | Gross | |
| 5,887,752 A * | 3/1999 | Strother | 222/1 |
| 5,933,287 A | 8/1999 | Muller | |
| 5,951,523 A | 9/1999 | Osterlind et al. | |
| 5,954,697 A | 9/1999 | Srisathapat et al. | |
| 5,957,889 A | 9/1999 | Poulsen et al. | |
| 5,984,894 A | 11/1999 | Poulsen et al. | |
| 5,997,501 A | 12/1999 | Gross et al. | |
| 6,003,736 A | 12/1999 | Ljunggren | |
| 6,033,377 A | 3/2000 | Rasmussen et al. | |
| 6,067,906 A * | 5/2000 | Ryan et al. | 101/335 |
| 6,088,608 A | 7/2000 | Schulman et al. | |
| 6,099,504 A | 8/2000 | Gross et al. | |
| 6,117,107 A | 9/2000 | Chen | |
| 6,119,028 A | 9/2000 | Schulman et al. | |
| 6,126,643 A | 10/2000 | Vaillancouert | |
| 6,186,982 B1 | 2/2001 | Gross et al. | |
| 6,229,584 B1 | 5/2001 | Chuo et al. | |
| 6,242,665 B1 | 6/2001 | Malowaniec | |
| 6,248,093 B1 | 6/2001 | Moberg | |
| 6,261,272 B1 | 7/2001 | Gross et al. | |
| 6,275,717 B1 | 8/2001 | Gross et al. | |
| 6,277,095 B1 | 8/2001 | Kriesel et al. | |
| 6,312,409 B1 | 11/2001 | Gross | |
| 6,314,317 B1 | 11/2001 | Willis | |
| 6,346,095 B1 | 2/2002 | Gross et al. | |
| 6,364,865 B1 | 4/2002 | Lavi et al. | |
| 6,375,047 B1 * | 4/2002 | Herda et al. | 222/389 |
| 6,406,455 B1 | 6/2002 | Willis et al. | |
| 6,423,035 B1 | 7/2002 | Das et al. | |
| 6,440,096 B1 | 8/2002 | Lastovich et al. | |
| 6,450,993 B1 | 9/2002 | Lin | |
| 6,461,329 B1 | 10/2002 | Van Antwerp et al. | |
| 6,474,219 B2 | 11/2002 | Klitmose et al. | |
| 6,474,375 B2 * | 11/2002 | Spero et al. | 141/329 |
| 6,478,771 B1 | 11/2002 | Lavi et al. | |
| 6,485,461 B1 | 11/2002 | Mason et al. | |
| 6,485,465 B2 | 11/2002 | Moberg et al. | |
| 6,490,483 B2 | 12/2002 | Willis | |
| 6,503,225 B1 | 1/2003 | Kirsch et al. | |
| 6,508,788 B2 | 1/2003 | Preuthun | |
| 6,537,251 B2 | 3/2003 | Klitmose | |
| 6,551,285 B1 | 4/2003 | Bierman | |
| 6,572,600 B1 | 6/2003 | Roe et al. | |
| 6,585,707 B2 | 7/2003 | Cabiri et al. | |
| 6,589,229 B1 | 7/2003 | Connelly et al. | |
| 6,595,956 B1 | 7/2003 | Gross et al. | |
| 6,607,509 B2 | 8/2003 | Bobroff et al. | |
| 6,607,513 B1 | 8/2003 | Down et al. | |
| 6,613,019 B2 | 9/2003 | Munk | |
| 6,616,627 B2 | 9/2003 | Willis et al. | |
| 6,626,874 B1 | 9/2003 | Duchamp | |
| 6,641,565 B1 | 11/2003 | Lavi et al. | |
| 6,641,566 B2 | 11/2003 | Douglas et al. | |
| 6,645,181 B1 | 11/2003 | Lavi et al. | |
| 6,656,147 B1 | 12/2003 | Wilkinson et al. | |
| 6,656,158 B2 | 12/2003 | Gregory et al. | |
| 6,656,159 B2 | 12/2003 | Flaherty | |
| 6,669,669 B2 | 12/2003 | Flaherty et al. | |
| 6,689,100 B2 | 2/2004 | Connelly et al. | |
| 6,692,457 B2 | 2/2004 | Flaherty | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,195 B2 | 4/2004 | Nolan, Jr. et al. | |
| 6,719,734 B1 | 4/2004 | Harkless | |
| 6,723,068 B2 | 4/2004 | Lavi et al. | |
| 6,723,072 B2 | 4/2004 | Flaherty et al. | |
| 6,740,059 B2 | 5/2004 | Flaherty | |
| 6,740,072 B2 | 5/2004 | Starkweather et al. | |
| 6,749,587 B2 | 6/2004 | Flaherty | |
| 6,767,188 B2 | 7/2004 | Vrane et al. | |
| 6,768,425 B2 | 7/2004 | Flaherty et al. | |
| 6,786,246 B2 | 9/2004 | Ohms et al. | |
| 6,796,965 B2 | 9/2004 | Dumaresq-Lucas et al. | |
| 6,808,506 B2 | 10/2004 | Lastovich et al. | |
| 6,827,702 B2 | 12/2004 | Lebel et al. | |
| 6,830,558 B2 | 12/2004 | Flaherty et al. | |
| 6,830,560 B1 | 12/2004 | Gross et al. | |
| 6,886,724 B2 | 5/2005 | Hung | |

| | | |
|---|---|---|
| 6,899,699 B2 | 5/2005 | Enggaard |
| 6,915,147 B2 | 7/2005 | Lebel et al. |
| 6,918,887 B1 * | 7/2005 | Gremel et al. .............. 604/6.09 |
| 6,936,006 B2 | 8/2005 | Sabra |
| 6,939,324 B2 | 9/2005 | Gonnelli et al. |
| 6,948,522 B2 * | 9/2005 | Newbrough et al. ......... 137/550 |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,220,245 B2 | 5/2007 | Kriesel |
| 7,220,889 B2 | 5/2007 | Sigurjonsson et al. |
| 7,318,816 B2 | 1/2008 | Bobroff et al. |
| 7,323,142 B2 | 1/2008 | Pendo et al. |
| 7,390,294 B2 | 6/2008 | Hassler, Jr. |
| 7,399,484 B2 | 7/2008 | Ellefson et al. |
| 7,621,429 B2 * | 11/2009 | Wu et al. ...................... 222/389 |
| 7,686,787 B2 | 3/2010 | Moberg et al. |
| 7,858,112 B2 | 12/2010 | Hatanaka et al. |
| 7,981,085 B2 * | 7/2011 | Ethelfeld ...................... 604/157 |
| 2001/0041869 A1 | 11/2001 | Causey, III et al. |
| 2002/0040208 A1 | 4/2002 | Flaherty et al. |
| 2002/0072733 A1 | 6/2002 | Flaherty |
| 2002/0104584 A1 * | 8/2002 | Spero et al. .................. 141/329 |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0023206 A1 | 1/2003 | Bausmith, III et al. |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0104032 A1 | 6/2003 | Sawhney et al. |
| 2003/0125672 A1 | 7/2003 | Adair et al. |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0212364 A1 | 11/2003 | Mann et al. |
| 2003/0229310 A1 | 12/2003 | Flaherty et al. |
| 2003/0233069 A1 | 12/2003 | Gillespie et al. |
| 2004/0002682 A1 | 1/2004 | Kovelman et al. |
| 2004/0010207 A1 | 1/2004 | Flaherty et al. |
| 2004/0011866 A1 | 1/2004 | Saad |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0073095 A1 | 4/2004 | Causey, III et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0140327 A1 * | 7/2004 | Osborne et al. ............. 222/386.5 |
| 2004/0158207 A1 | 8/2004 | Hunn et al. |
| 2004/0199140 A1 | 10/2004 | Rue et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0236201 A1 | 11/2004 | Lebel et al. |
| 2004/0260233 A1 | 12/2004 | Garibotto et al. |
| 2005/0022274 A1 | 1/2005 | Campbell et al. |
| 2005/0065760 A1 | 3/2005 | Murtfeldt et al. |
| 2005/0101920 A1 | 5/2005 | Keane et al. |
| 2005/0119618 A1 | 6/2005 | Gonnelli |
| 2005/0137530 A1 | 6/2005 | Campbell et al. |
| 2006/0184119 A1 | 8/2006 | Remde et al. |
| 2006/0253085 A1 | 11/2006 | Geismar et al. |
| 2006/0264835 A1 | 11/2006 | Nielsen et al. |
| 2006/0264894 A1 | 11/2006 | Moberg et al. |
| 2007/0062068 A1 | 3/2007 | Li |
| 2007/0066939 A1 | 3/2007 | Krulevitch et al. |
| 2007/0073235 A1 | 3/2007 | Estes et al. |
| 2007/0293826 A1 | 12/2007 | Wall et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0257916 A1 * | 10/2008 | Chang ........................... 222/394 |
| 2008/0269682 A1 | 10/2008 | Kavazov et al. |
| 2009/0206111 A1 * | 8/2009 | Conrardy et al. ......... 222/386.5 |

FOREIGN PATENT DOCUMENTS

| | | |
|---|---|---|
| EP | 1 462 134 A1 | 9/2004 |
| EP | 1 527 792 A1 | 5/2005 |
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| FR | 1.496.026 | 9/1967 |
| GB | 1 452 104 | 10/1976 |
| GB | 2 176 711 A | 1/1987 |
| GB | 2 207 652 A | 2/1989 |
| WO | WO-95/23015 | 11/1995 |
| WO | WO 95/32015 | 11/1995 |
| WO | WO 96/26702 | 9/1996 |
| WO | WO 97/44078 | 11/1997 |
| WO | WO 97/46203 | 12/1997 |
| WO | WO 99/48546 | 9/1999 |
| WO | WO-99/59665 | 11/1999 |
| WO | WO-00/47254 | 8/2000 |
| WO | WO 00/69488 | 12/2000 |
| WO | WO 01/070307 | 9/2001 |
| WO | WO-01/76684 A1 | 10/2001 |
| WO | WO 02/02165 A2 | 1/2002 |
| WO | WO-02/20073 A2 | 3/2002 |
| WO | WO-02/28454 A2 | 4/2002 |
| WO | WO-02/40083 A2 | 5/2002 |
| WO | WO-02/49509 A2 | 6/2002 |
| WO | WO-02/068015 A2 | 9/2002 |
| WO | WO-03/006090 A1 | 1/2003 |
| WO | WO-03/024504 A2 | 3/2003 |
| WO | WO 03/026728 A1 | 4/2003 |
| WO | WO-03/033051 A1 | 4/2003 |
| WO | WO-03/059372 A3 | 7/2003 |
| WO | WO 03/072172 A2 | 9/2003 |
| WO | WO-03/074121 a1 | 9/2003 |
| WO | WO-03/090509 A2 | 11/2003 |
| WO | WO-03/090819 A2 | 11/2003 |
| WO | WO-03/090838 A1 | 11/2003 |

| | | |
|---|---|---|
| WO | WO-03/103758 A1 | 12/2003 |
| WO | WO-03/103763 A1 | 12/2003 |
| WO | WO 2004/006981 A2 | 1/2004 |
| WO | WO-2004/006982 A2 | 1/2004 |
| WO | WO 2004/030716 | 4/2004 |
| WO | WO 2004/030717 | 4/2004 |
| WO | WO-2004/047641 A2 | 6/2004 |
| WO | WO-2004/060436 A2 | 7/2004 |
| WO | WO-2004/093648 A2 | 11/2004 |
| WO | WO-2004/098390 A2 | 11/2004 |
| WO | WO-2004/098454 A2 | 11/2004 |
| WO | WO 2004/098683 A1 | 11/2004 |
| WO | WO 2004098683 A1 * | 11/2004 |
| WO | WO 2004/110526 A1 | 12/2004 |
| WO | WO 2005/000382 A2 | 1/2005 |
| WO | WO 2005/072795 A2 | 8/2005 |
| WO | WO-2005/094920 A1 | 10/2005 |
| WO | WO 2005/097237 A1 | 10/2005 |
| WO | WO-2006/015922 A1 | 2/2006 |
| WO | WO-2006/018425 A3 | 2/2006 |
| WO | WO-2006/018447 A3 | 2/2006 |
| WO | WO-2006/024671 A1 | 3/2006 |
| WO | WO-2006/024672 A1 | 3/2006 |
| WO | WO-2006/032692 A1 | 3/2006 |
| WO | WO-2006/042811 A3 | 4/2006 |
| WO | WO 2006/058435 A2 | 6/2006 |
| WO | WO-2006/072416 A2 | 7/2006 |
| WO | WO-2006/075016 A1 | 7/2006 |
| WO | WO-2006/077262 A1 | 7/2006 |
| WO | WO-2006/077263 A1 | 7/2006 |
| WO | WO-2006/084464 A1 | 8/2006 |
| WO | WO-2006/086980 A1 | 8/2006 |
| WO | WO-2006/089547 A1 | 8/2006 |
| WO | WO-2006/089548 A1 | 8/2006 |
| WO | WO-2006/089965 A1 | 8/2006 |
| WO | WO-2006/096746 A1 | 9/2006 |
| WO | WO-2006/097453 A1 | 9/2006 |
| WO | WO-2006/104806 A2 | 10/2006 |
| WO | WO-2006/108775 A2 | 10/2006 |
| WO | WO-2006/108809 A1 | 10/2006 |
| WO | WO-2006/116997 A1 | 11/2006 |
| WO | WO-2006/120253 A2 | 11/2006 |
| WO | WO-2006/125692 A1 | 11/2006 |
| WO | WO-2007/000425 A2 | 1/2007 |
| WO | WO-2007/000426 A2 | 1/2007 |
| WO | WO-2007/000427 A1 | 1/2007 |
| WO | WO-2007/038091 A2 | 4/2007 |
| WO | WO 2007062068 A2 | 5/2007 |
| WO | WO-2007/071255 A1 | 6/2007 |
| WO | WO-2007/076641 A1 | 7/2007 |
| WO | WO-2007/087808 A1 | 8/2007 |
| WO | WO 2007/130809 A2 | 11/2007 |
| WO | WO 2008/024614 A2 | 2/2008 |
| WO | WO 2008/093063 A2 | 8/2008 |
| WO | WO 2008/151241 A2 | 12/2008 |

OTHER PUBLICATIONS

Office Action dated Dec. 30, 2010 from related U.S. Appl. No. 12/107,580.
Office Action dated Dec. 9, 2010 from related U.S. Appl. No. 12/099,738.
PCT Search Report Dated Jun. 5,.2009 from related PCT application No. PCT/US2008/082187.
Office Action dated Apr. 30, 2009 from related U.S. Appl. No. 12/027,963.
Office Action dated Jul. 8, 2009 from related U.S. Appl. No. 11/964,649.
Office Action dated Jul. 10, 2009 from related U.S. Appl. No. 12/411,236.
Office Action dated Aug. 4, 2009 from related U.S. Appl. No. 12/411,247.
US Office Action dated Aug. 18, 2010 from related U.S. Appl. No. 12/107,580.
Final Office Action dated Jan. 14, 2010 from related U.S. Appl. No. 12/411,247.
Office Action dated Jan. 7, 2010 from related U.S. Appl. No. 11/964,649.
Office Action dated Mar. 4, 2010 from related U.S. Appl. No. 12/099,738.
US Office Action dated Nov. 10, 2009 fron related U.S. Appl. No. 12/099,738.
US Office Action for U.S. Appl. No. 12/027,963 dated Sep. 24, 2009.
US Office Action for U.S. Appl. No. 12/411,236 dated Oct. 23, 2009.
US Office Action dated Mar. 29, 2011 from related U.S. Appl. No. 11/964,649.
US Notice of Allowance dated Jul. 27, 2011 from related U.S. Appl. No. 12/411,247.
PCT search report dated Feb. 3, 2009 from PCT Application No. PCT/US2008/082185.
Partial PCT Search Report (Invitation to Pay Additional Fees) dated Feb. 2, 2009 for related PCT application No. PCT/US2008/082186.
U.S. Appl. No. 09/360,342, filed Jul. 22, 1999, ALfred E. Mann Foundation for Scientific Research.
PCT Search Report dated May 15, 2008 for PCT application No. PCT/US2007/076679.
U.S Office Action dated Mar. 8, 2011 from related U.S. Appl. No. 12/411,247.
US Notice of Allowance dated Mar. 3, 2011 from related U.S. Appl. No. 12/107,580.
US Office Action dated Feb. 23, 2011 from related U.S. Appl. No. 12/411,236.
Partial PCT Search Report dated Mar. 5, 2009 from related PCT application No. PCT/US2008/082187.
PCT Search Report dated Apr. 28, 2009 from related PCT application No. PCT/US2008/082186.
Office Action Dated Jan. 29, 2009 from related U.S. Appl. No. 11/604,172.
Office Action Dated Nov. 24, 2008 from related U.S. Appl. No. 11/759,725.
Office Action Dated Apr. 10, 2009 from related U.S. Appl. No. 11/588,832.
Office Action Dated Apr. 13, 2009 from related U.S. Appl. No. 11/604,171.
Office Action Dated Apr. 9, 2009 from related U.S. Appl. No. 11/515,225.
International Search Report and Written Opinion for PCT application No. PCT/US2008/082193 dated Jun. 29, 2010.
International Search Report and Written Opinion for related PCT Application No. PCT/US2007/076641 dated Feb. 27, 2008.
Office Action dated Jul. 21, 2010 from related U.S. Appl. No. 12/099,738.
Office Action dated Jun. 16, 2010 from related U.S. Appl. No. 12/027,963.
US Office Action dated Oct. 1, 2010 U.S. Appl. No. 12/411,247.
US Office Action dated Sep. 28, 2010 from related U.S. Appl. No. 12/411,236.
US Office Action dated Oct. 15, 2010 from related U.S. Appl. No. 12/027,963.
US Office Action from related U.S. Appl. No. 12/099,738, mailed Dec. 20, 2012, 27 pages.
US Office Action from related U.S. Appl. No. 13/083,512, mailed Nov. 28, 2012, 26 pages.

* cited by examiner

SYSTEMS AND METHODS FOR RESERVOIR FILLING

CROSS-REFERENCE TO RELATED PATENT APPLICATIONS

Embodiments of the present invention relate to U.S. Provisional Application Ser. No. 60/927,032, filed Apr. 30, 2007, entitled "Needle Inserting, Reservoir Filling, Bubble Management, Fluid Flow Connections and Infusion Medium Delivery Systems and Methods with Same", the entire contents of which are incorporated by reference herein and which is a basis for a claim of priority.

Embodiments of the present invention relate to PCT International Application No. PCT/US2007/076641, filed Aug. 23, 2007, the entire contents of which are incorporated by reference herein, and which claims the benefit of U.S. Provisional Application Ser. No. 60/927,032, filed Apr. 30, 2007.

BACKGROUND OF THE INVENTION

1. Field of the Invention

Embodiments of the present invention relate generally to systems and methods for limiting a presence of air bubbles in a fluidic medium filled into a reservoir.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have also been configured in implantable devices, which are implanted inside of the body of a patient. External pump type delivery devices include devices designed for use in a stationary location, such as a hospital, a clinic, or the like, and further include devices configured for ambulatory or portable use, such as devices that are designed to be carried by a patient, or the like. External pump type delivery devices may be connected in fluid flow communication to a patient or user, for example, through a suitable hollow tubing. The hollow tubing may be connected to a hollow needle that is designed to pierce the skin of the patient and to deliver a fluidic medium therethrough. Alternatively, the hollow tubing may be connected directly to the patient as through a cannula, or the like.

Examples of some external pump type delivery devices are described in the following references: (i) Published PCT Application WO 01/70307 (PCT/US01/09139), entitled "Exchangeable Electronic Cards for Infusion Devices"; (ii) Published PCT Application WO 04/030716 (PCT/US2003/028769), entitled "Components and Methods for Patient Infusion Device"; (iii) Published PCT Application WO 04/030717 (PCT/US2003/029019), entitled "Dispenser Components and Methods for Infusion Device"; (iv) U.S. Patent Application Pub. No. 2005/0065760, entitled "Method for Advising Patients Concerning Doses Of Insulin"; and (v) U.S. Pat. No. 6,589,229, entitled "Wearable Self-Contained Drug Infusion Device", each of which is incorporated by reference herein in its entirety.

As compared to syringes and insulin pens, pump type delivery devices can be significantly more convenient to a patient, in that doses of insulin may be calculated and delivered automatically to a patient at any time during the day or night. Furthermore, when used in conjunction with glucose sensors or monitors, insulin pumps may be automatically controlled to provide appropriate doses of a fluidic medium at appropriate times of need, based on sensed or monitored levels of blood glucose. As a result, pump type delivery devices have become an important aspect of modern medical treatments of various types of medical conditions, such as diabetes, and the like. As pump technologies improve and doctors and patients become more familiar with such devices, external medical infusion pump treatments are expected to increase in popularity and are expected to increase substantially in number over the next decade.

SUMMARY OF THE DISCLOSURE

Various embodiments of the present invention are directed to limiting a presence of air bubbles in a fluidic medium filled into a reservoir. In various embodiments, a fluidic medium is forced from a vial into a reservoir. Also, in various embodiments, a vial is degassed prior to being used to fill a reservoir. In some embodiments, a filling process is automated and, in some embodiments, a membrane is located in a fluid flow path to trap air bubbles in a fluidic medium being filled into a reservoir.

A system in accordance with an embodiment of the present invention includes a vial. In various embodiments, the vial includes a diaphragm that separates a fillable volume of the vial from a pressurizable volume of the vial, where the diaphragm is inflatable to reduce the fillable volume in a case where a pressure within the pressurizable volume is increased. In some embodiments, the diaphragm is deflatable to increase the fillable volume in a case where the pressure within the pressurizable volume is decreased. Also, in some embodiments, the diaphragm is attached to an inner surface of the vial.

In various embodiments, the system further includes a pressure providing device for changing a pressure within the pressurizable volume. In some embodiments, the pressure providing device includes a syringe, and the syringe is connectable to the vial such that in a case where the syringe is filled with air and is connected to the vial and a plunger head within the syringe is advanced, a pressure within the pressurizable volume is increased so as to cause the diaphragm to inflate and reduce the fillable volume. Also, in some embodiments, the fillable volume is fillable with a fluidic medium.

In various embodiments, the system further includes a reservoir having an interior volume. In some embodiments, the diaphragm is deflatable to evacuate air from the interior volume of the reservoir into the fillable volume of the vial in a case where the interior volume of the reservoir and the fillable volume of the vial are connected by a needle and a vacuum is applied to the pressurizable volume of the vial. Also, in some embodiments, the diaphragm is inflatable to force a fluidic medium out of the fillable volume of the vial and into the interior volume of the reservoir in a case where the fillable volume of the vial is holding the fluidic medium and the fillable volume of the vial is connected to the interior volume of the reservoir by a needle and the pressure within the pressurizable volume is increased.

In various embodiments, the system further includes a membrane located in a flow path between the fillable volume of the vial and the interior volume of the reservoir for trapping bubbles in the fluidic medium in a case where the fluidic medium is transferred from the fillable volume of the vial to the interior volume of the reservoir. Also, in various embodiments, the vial further includes a first port for allowing a fluidic medium to flow out of the fillable volume of the vial and a second port for allowing a gas to be injected into the pressurizable volume of the vial.

A method in accordance with an embodiment of the present invention includes providing a fluid flow path between a fillable volume of a vial and an interior volume of a reservoir, and applying a pressure to a pressurizable volume of the vial so as to inflate a diaphragm to cause a fluidic medium to be expelled from the fillable volume of the vial into the interior volume of the reservoir. In various embodiments, the applying the pressure includes injecting at least one of a gas and a liquid from a pressure providing device into the pressurizable volume of the vial. In some embodiments, the pressure providing device includes a syringe, and the injecting includes injecting the at least one of the gas and the liquid from the syringe into the pressurizable volume of the vial by advancing a plunger head within the syringe.

In various embodiments, the method further includes applying a vacuum to the pressurizable volume of the vial so as to deflate the diaphragm to cause air to be evacuated from the interior volume of the reservoir into the fillable volume of the vial. In some embodiments, the applying the vacuum occurs before the applying the pressure. Also, in some embodiments, the method further includes trapping air bubbles in the fluidic medium by a membrane when the fluidic medium is transferred from the fillable volume of the vial to the interior volume of the reservoir.

A system in accordance with an embodiment of the present invention includes a vial having an interior volume for containing a fluidic medium, and a moveable element located within the vial, where the moveable element is advancable within the vial to reduce the interior volume. In various embodiments, the moveable element is retractable within the vial to increase the interior volume. In some embodiments, the vial has a barrel portion and a curved portion, the moveable element has a barrel portion with an outer contour that substantially matches an inner contour of the barrel portion of the vial, and the moveable element has a curved portion with an outer contour that substantially matches an inner contour of the curved portion of the vial. Also, in some embodiments, the system further includes a transfer guard for providing a fluid flow path from the vial to a reservoir, where the transfer guard includes a membrane in the fluid flow path for trapping air bubbles.

A method in accordance with an embodiment of the present invention includes providing a fluid flow path between an interior volume of a vial and an interior volume of a reservoir, and advancing a moveable element within the vial to cause a fluidic medium within the interior volume of the vial to be transferred to the interior volume of the reservoir through the fluid flow path. In various embodiments, the advancing includes advancing the moveable element within the vial until a curved portion of the moveable element contacts a curved portion of the vial. In some embodiments, the method further includes trapping air bubbles in the fluidic medium by a membrane located in the fluid flow path.

A degassing tool in accordance with an embodiment of the present invention includes a plunger housing having a port, a plunger head moveable within the plunger housing, a plunger arm connected to the plunger head, a first arm connected to the plunger arm, a first handle, a second handle, and a pivot member. The first handle and the second handle and the first arm are connected to the pivot member such that in a case where the first handle is pivoted toward the second handle, the first arm is pivoted and moves the plunger arm to cause the plunger head to retract within the plunger housing so as to increase a volume in the plunger housing between the plunger head and the port.

In various embodiments, the first handle and the second handle and the first arm are connected to the pivot member such that in a case where the first handle is pivoted away from the second handle, the first arm is pivoted and moves the plunger arm to cause the plunger head to advance within the plunger housing so as to decrease a volume in the plunger housing between the plunger head and the port. In some embodiments, the degassing tool further includes an insertion member, connected to the port of the plunger housing, for piercing a septum of a vial. Also, in some embodiments, the degassing tool further includes a second arm for holding a vial, where the second arm is connected to the second handle such that the second arm does not pivot with a pivoting of the pivot member.

A method of degassing a vial with a degassing tool in accordance with an embodiment of the present invention includes piercing a septum of the vial with an insertion member of the degassing tool that is connected to a port of a plunger housing of the degassing tool, and pivoting a first handle of the degassing tool toward a second handle of the degassing tool so as to pivot a first arm of the degassing tool to move a plunger arm of the degassing tool to cause a plunger head of the degassing tool to retract within the plunger housing so as to increase a volume in the plunger housing between the plunger head and the port. Gas is extracted from the vial and into the plunger housing through the insertion member when the volume in the plunger housing between the plunger head and the port is increased.

An apparatus in accordance with an embodiment of the present invention includes a transfer guard, a plunger housing, a plunger head, a plunger arm, and a pressure providing device. The transfer guard allows for providing a fluid flow path from a vial to a reservoir. The plunger housing is connected to the transfer guard. The plunger head is moveable within the plunger housing. The plunger arm has a first end connected to the plunger head and a second end that is connectable to a reservoir plunger arm that is connected to a reservoir plunger head within the reservoir. The pressure providing device allows for providing a pressure to the plunger head to move the plunger head within the plunger housing so as to move the plunger arm. When the plunger arm is connected to the reservoir plunger arm and the plunger arm is moved, the reservoir plunger arm moves so as to move the reservoir plunger head within the reservoir.

A method in accordance with an embodiment of the present invention allows for filling a reservoir from a vial using an apparatus. The apparatus includes a transfer guard, a plunger housing connected to the transfer guard, a plunger head within the plunger housing, a plunger arm connected to the plunger head, and a pressure providing device. In various embodiments, the method includes connecting the vial and the reservoir to the transfer guard to provide a fluid flow path from the vial to the reservoir, connecting the plunger arm of the apparatus to a reservoir plunger arm that is connected to a reservoir plunger head within the reservoir, and providing pressure by the pressure providing device to the plunger head within the plunger housing to move the plunger head within the plunger housing so as to move the plunger arm. When the plunger arm is connected to the reservoir plunger arm and the plunger arm is moved, the reservoir plunger arm moves so as to move the reservoir plunger head within the reservoir to allow a fluidic medium to flow from the vial to the reservoir through the fluid flow path.

An apparatus in accordance with an embodiment of the present invention includes a transfer guard, a pressure channel, a plunger head, and an air path member. The transfer guard allows for providing a fluid flow path from a vial to a reservoir. The pressure channel is connected to the transfer guard. The plunger head is moveable within the pressure channel. The air path member allows for providing an air path from the pressure channel to the vial. In a case where the vial and the reservoir are connected to the transfer guard and the plunger head is advanced within the pressure channel, air is forced from the pressure channel to the vial through the air path member to increase a pressure within the vial so as to force a fluidic medium from the vial to the reservoir through the fluid flow path.

A method in accordance with an embodiment of the present invention allows for filling a reservoir from a vial using an apparatus. The apparatus includes a transfer guard, a pressure channel connected to the transfer guard, a plunger head moveable within the pressure channel, and an air path member. In various embodiments, the method includes inserting an end of the air path member into the vial, connecting the vial and the reservoir to the transfer guard to provide a fluid flow path from the vial to the reservoir, and advancing the plunger head within the pressure channel to force air from the pressure channel into the vial through the air path member so as to increase a pressure within the vial to force a fluidic medium from the vial to the reservoir through the fluid flow path.

A transfer guard in accordance with an embodiment of the present invention includes a reservoir nest, a vial nest, a vacuum plunger nest, a first valve, a second valve, and a third valve. The reservoir nest allows for receiving a port of a reservoir. The vial nest allows for receiving a port of a vial. The vacuum plunger nest allows for receiving a port of a vacuum plunger. The first valve is moveable between at least an open position and a closed position for selectively opening and closing a fluid path to the reservoir nest. The second valve is moveable between at least an open position and a closed position for selectively opening and closing a fluid path to the vial nest. The third valve is moveable between at least an open position and a closed position for selectively opening and closing a fluid path to the vacuum plunger nest.

A method in accordance with an embodiment of the present invention includes placing a port of a reservoir in a reservoir nest of a transfer guard, placing a port of a vial in a vial nest of the transfer guard, placing a port of a vacuum plunger in a vacuum plunger nest of the transfer guard, closing a first valve of the transfer guard to close a fluid path to the reservoir nest, opening a second valve of the transfer guard to open a fluid path to the vial nest, opening a third valve of the transfer guard to open a fluid path to the vacuum plunger nest, and drawing a fluidic medium from the vial into the vacuum plunger through the transfer guard. In various embodiments, the method further includes closing the second valve to close the fluid path to the vial nest, opening the first valve to open the fluid path to the reservoir nest, and expelling the fluidic medium from the vacuum plunger into the reservoir through the transfer guard.

A system in accordance with an embodiment of the present invention includes a pressure source, a filter connectable to a port of a reservoir for filtering air bubbles from a fluidic medium, an air needle for providing an air path between the pressure source and a vial, and a fluid needle for providing a fluid path between the vial and the filter.

A method in accordance with an embodiment of the present invention includes connecting a filter to a port of a reservoir, providing an air path between a pressure source and a vial, providing a fluid path between the vial and the filter, and forcing air from the pressure source to the vial through the air path so as to cause a fluidic medium in the vial to be expelled from the vial to the reservoir through the fluid path and the filter.

A system in accordance with an embodiment of the present invention includes a vial, an air sack, an air line, a one-way valve, and a drive mechanism. The vial has an interior volume for containing a fluidic medium. The air sack allows for holding air. The air line is connected between the air sack and the interior volume of the vial. The one-way valve is configured to allow air to pass from the air sack to the interior volume of the vial through the air line when the air sack is compressed. The drive mechanism is controllable to compress the air sack. A system in accordance with another embodiment of the present invention includes a reservoir sack, a one-way valve, and a pressure sack. The reservoir sack allows for containing a fluidic medium, and the reservoir sack has an outlet path. The pressure sack allows for forcing air through the one-way valve and into the reservoir sack so as to cause the fluidic medium to be expelled from the reservoir sack through the outlet path.

A system in accordance with an embodiment of the present invention includes a reservoir, a plunger head, a plunger rod, and a needle. The reservoir has a septum. The plunger head includes a plunger head septum. The plunger rod is connected to the plunger head, and the plunger rod includes a pressurized vessel that contains air under pressure. The needle has a first end for piercing a septum of a vial, and has a second end for piercing the septum of the reservoir and the plunger head septum so as to provide an air path between the pressurized vessel in the plunger rod and the vial. A system in accordance with another embodiment of the present invention includes a reservoir, a plunger head, a plunger head septum, and a plunger rod. The plunger head is moveable within the reservoir, and the plunger head has a channel from a first surface of the plunger head to a second surface of the plunger head. The plunger head septum is located within the channel of the plunger head. The plunger rod is connected to the plunger head, and the plunger rod has a hollow interior for allowing a needle to pass within the plunger rod and through the plunger head septum.

DETAILED DESCRIPTION OF PREFERRED EMBODIMENTS

Figure 1:
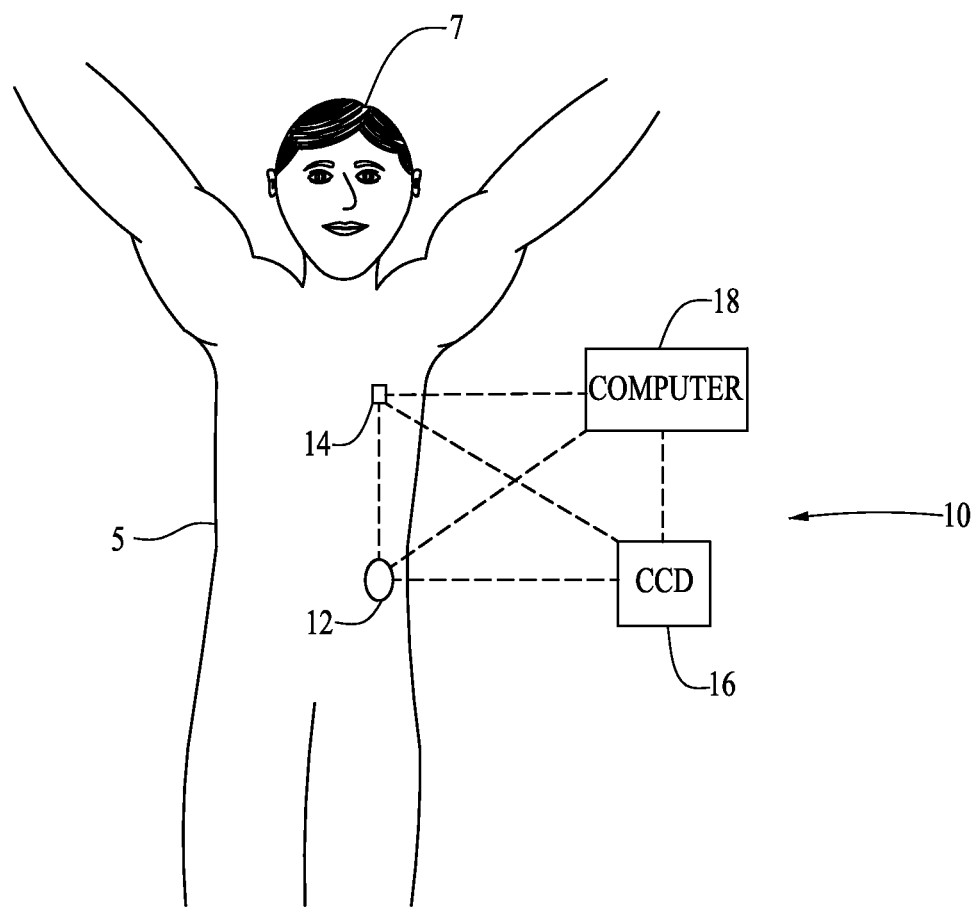
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user 7. The locations at which the delivery device 12 and the sensing device 14 are secured to the body 5 of the user 7 in FIG. 1 are provided only as representative, non-limiting, examples.

In some embodiments, the system 10, delivery device 12, sensing device 14, CCD 16, and computer 18 may be similar to those described in the following U.S. Patent Applications that were assigned to the assignee of the present invention, however, there may be different reservoir and/or plunger configurations such as described herein, where each of the following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; (xv) U.S. patent application Ser. No. 11/645,993, filed Dec. 26, 2006, "Infusion Medium Delivery Device And Method With Compressible Or Curved Reservoir Or Conduit"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/636,384, filed Dec. 8, 2006, "Infusion Medium Delivery Device And Method With Compressible Or Curved Reservoir Or Conduit"; and (xxi) U.S. patent application Ser. No. 11/645,972, filed Dec. 26, 2006, "Infusion Medium Delivery System, Device And Method With Needle Inserter And Needle Inserter Device And Method". In other embodiments, the system 10, delivery device 12, sensing device 14, CCD 16, and computer 18 may have other suitable configurations.

The delivery device 12 is configured to deliver a fluidic medium to the body 5 of the user 7. In various embodiments, the fluidic medium includes a liquid, a fluid, a gel, or the like. In some embodiments, the fluidic medium includes a medicine or a drug for treating a disease or a medical condition. For example, the fluidic medium may include insulin for treating diabetes, or may include a drug for treating pain, cancer, a pulmonary disorder, HIV, or the like. In some embodiments, the fluidic medium includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user 7. For example, the sensing device 14 may include electronics and enzymes reactive to a biological condition, such as a blood glucose level, or the like, of the user 7. In various embodiments, the sensing device 14 may be secured to the body 5 of the user 7 or embedded in the body 5 of the user 7 at a location that is remote from the location at which the delivery device 12 is secured to the body 5 of the user 7. In various other embodiments, the sensing device 14 may be incorporated within the delivery device 12.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user 7, such as, but not limited to, blood glucose level, or the like. The delivery device 12 may be configured to deliver fluidic media in response to the condition sensed by the sensing device 14. In turn, the sensing device 14 may continue to sense a new condition of the user 7, allowing the delivery device 12 to deliver fluidic media continuously in response to the new condition sensed by the sensing device 14 indefinitely. In other embodiments, the sensing device 14 and/or the delivery device 12 may be configured to utilize the closed-loop system only for a portion of the day, for example only when the user 7 is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver the fluidic medium to the body 5 of the user 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. Also, in various embodiments, the delivery device 12 and/or the sensing device 14 may be configured to transmit data to the CCD 16 and/or the computer 18 for display or processing of the data by the CCD 16 and/or the computer 18. Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same", all of which are incorporated herein by reference in their entirety.

Figure 2:
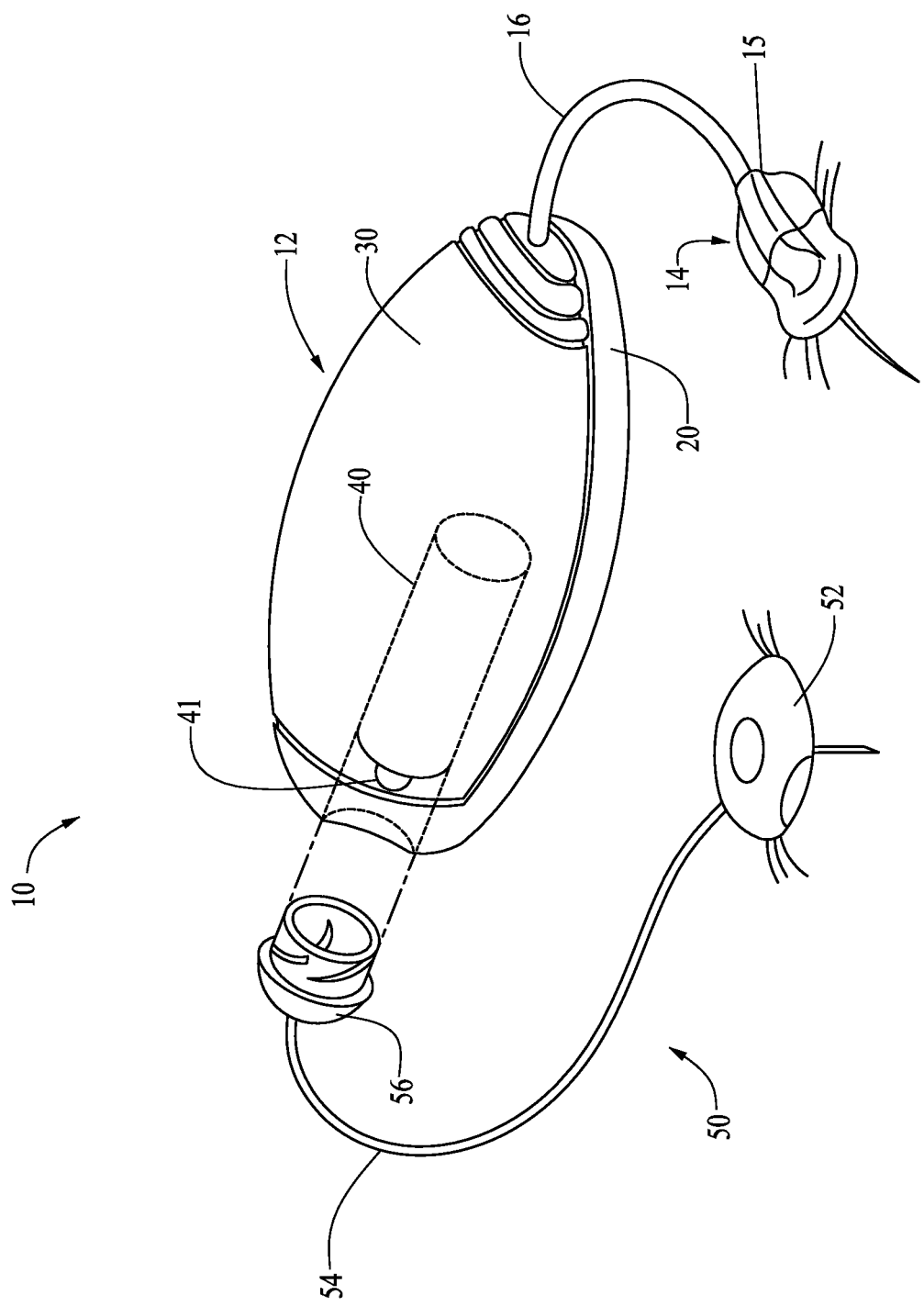
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir 40. The delivery device 12 may further include an infusion path 50.

Elements of the delivery device 12 that ordinarily contact the body of a user or that ordinarily contact a fluidic medium during operation of the delivery device 12 may be considered as a disposable portion of the delivery device 12. For example, a disposable portion of the delivery device 12 may include the disposable housing 20 and the reservoir 40. The disposable portion of the delivery device 12 may be recommended for disposal after a specified number of uses.

On the other hand, elements of the delivery device 12 that do not ordinarily contact the body of the user or the fluidic medium during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user or the fluidic medium during normal operation of the delivery device 12 and, thus, may be retained for re-use with replaced disposable portions of the delivery device 12.

In various embodiments, the disposable housing 20 supports the reservoir 40 and has a bottom surface (facing downward and into the page in FIG. 2) that is configured to secure to the body of a user. An adhesive may be employed at an interface between the bottom surface of the disposable housing 20 and the skin of a user, so as to adhere the disposable housing 20 to the skin of the user. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user, for example against the skin of the user. Thus, in some embodiments, the delivery device 12 may be attached to the skin of the user.

In other embodiments, the disposable housing 20 and/or the remaining portions of the delivery device 12 may be worn or otherwise attached on or underneath clothing of the user. Similarly, the delivery device 12 may be supported by any suitable manner, such as, but not limited to, on a belt, in a pocket, and the like. Representative examples of such delivery devices 12 may include, but are not limited to, the MiniMed® Paradigm® 522 Insulin Pump, MiniMed® Paradigm® 722 Insulin Pump, MiniMed® Paradigm® 515 Insulin Pump, MiniMed® Paradigm® 715 Insulin Pump, MiniMed® Paradigm® 512R Insulin Pump, MiniMed® Paradigm® 712R Insulin Pump, MiniMed® 508 Insulin Pump, MiniMed® 508R Insulin Pump, and any other derivatives thereof.

The reservoir 40 is configured for containing or holding a fluidic medium, such as, but not limited to insulin. In various embodiments, the reservoir 40 includes a hollow interior volume for receiving the fluidic medium, such as, but not limited to, a cylinder-shaped volume, a tubular-shaped volume, or the like. In some embodiments, the reservoir 40 may be provided as a cartridge or canister for containing a fluidic medium. In various embodiments, the reservoir 40 is able to be refilled with a fluidic medium. In further embodiments, the reservoir 40 is pre-filled with a fluidic medium.

The reservoir 40 may be supported by the disposable housing 20 in any suitable manner. For example, the disposable housing 20 may be provided with projections or struts (not shown), or a trough feature (not shown), for holding the reservoir 40. In some embodiments, the reservoir 40 may be supported by the disposable housing 20 in a manner that allows the reservoir 40 to be removed from the disposable housing 20 and replaced with another reservoir. Alternatively, or in addition, the reservoir 40 may be secured to the disposable housing 20 by a suitable adhesive, a strap, or other coupling structure.

In various embodiments, the reservoir 40 includes a port 41 for allowing a fluidic medium to flow into and/or flow out of the interior volume of the reservoir 40. In some embodiments, the infusion path 50 includes a connector 56, a tube 54, and a needle apparatus 52. The connector 56 of the infusion path 50 may be connectable to the port 41 of the reservoir 40. In various embodiments, the disposable housing 20 is configured with an opening near the port 41 of the reservoir 40 for allowing the connector 56 of the infusion path 50 to be selectively connected to and disconnected from the port 41 of the reservoir 40.

In various embodiments, the port 41 of the reservoir 40 is covered with or supports a septum (not shown in FIG. 2), such as a self-sealing septum, or the like. The septum may be configured to prevent a fluidic medium from flowing out of the reservoir 40 through the port 41 when the septum is not pierced. Also, in various embodiments, the connector 56 of the infusion path 50 includes a needle for piercing the septum covering the port 41 of the reservoir 40 so as to allow the fluidic medium to flow out of the interior volume of the reservoir 40. Examples of needle/septum connectors can be found in U.S. patent application Ser. No. 10/328,393, filed Dec. 22, 2003, entitled "Reservoir Connector", which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user. Also, in various embodiments, the tube 54 connects the connector 56 with the needle apparatus 52 and is hollow, such that the infusion path 50 is able to provide a path to allow for the delivery of a fluidic medium from the reservoir 40 to the body of a user.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts. In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to the fluidic medium within the reservoir 40 to force the fluidic medium out of the reservoir 40 and into an infusion path, such as the infusion path 50, for delivery to a user. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir 40 and to drive the plunger head in a direction to force the fluidic medium out of the port 41 of the reservoir 40 and to the user. Also, in some embodiments, the motor may be controllable to reverse direction so as to move the plunger arm and the plunger head to cause fluid to be drawn into the reservoir 40 from a patient. The motor may be arranged within the durable housing 30 and the reservoir 40 may be correspondingly arranged on the disposable housing 20, such that the operable engagement of the motor with the plunger head, through the appropriate linkage, occurs automatically upon the user connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user, a greater level of user comfort may be achieved when the disposable housing 20 is secured to the skin of the user. Also, a flexible disposable housing 20 may result in an increase in site options on the body of the user at which the disposable housing 20 may be secured.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user. In other embodiments, the continuous glucose sensor may be located externally, for example on the skin of the user, or attached to clothing of the user. In such embodiments, fluid may be drawn continually from the user and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user or, in other embodiments, may be an implantable sensor that is located in an implant site within the body of the user. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user and enzymes and/or electronics reactive to a biological condition, such as blood glucose level or the like, of the user. In this manner, the delivery device 12 may be provided with sensor data from the sensor 15 secured to the user at a site remote from the location at which the delivery device 12 is secured to the user.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic medium delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user.

Figure 3:
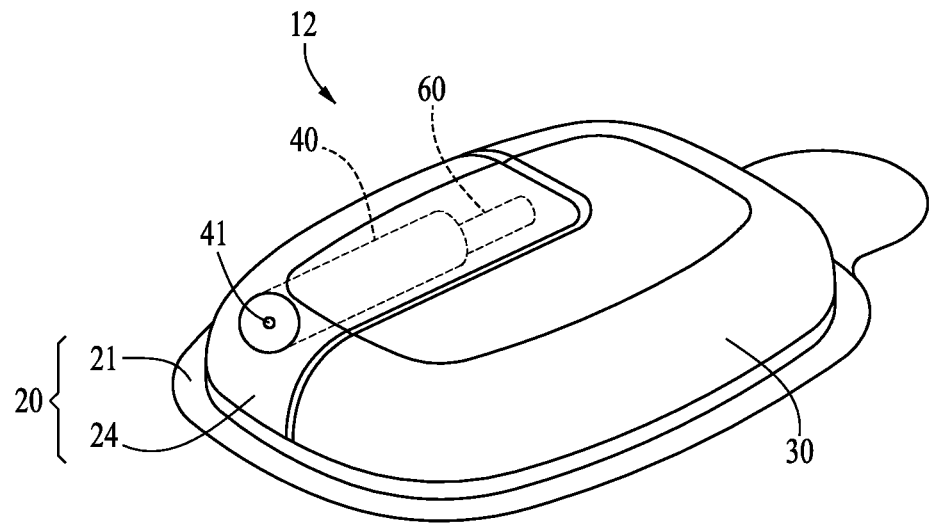
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir 40, the delivery device 12 in the embodiment of FIG. 3 provides for the durable housing 30 to secure to the disposable housing 20 without covering the reservoir 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In some embodiments, the base 21 and reservoir retaining portion 24 may be formed as a single, unitary structure.

The base 21 of the disposable housing 20 is configured to be secured to the body of a user. The reservoir retaining portion 24 of the disposable housing 20 is configured to house the reservoir 40. The reservoir retaining portion 24 of the disposable housing 20 may be configured to have an opening to allow for the port 41 of the reservoir 40 to be accessed from outside of the reservoir retaining portion 24 while the reservoir 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir 40.

Figure 4:
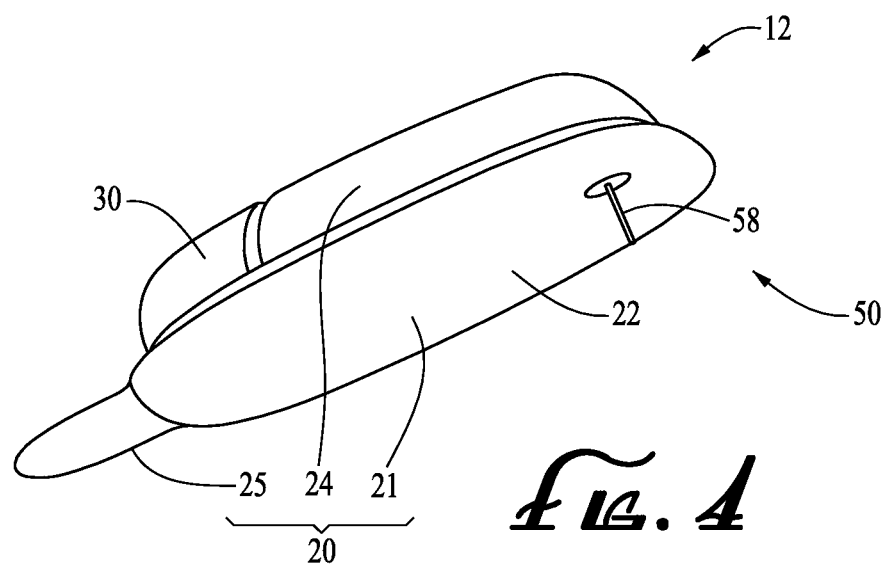
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user under the base 21, when extended. In this manner, the needle 58 may be used to pierce the skin of the user and deliver a fluidic medium to the user.

Alternatively, the needle 58 may be extended through a hollow cannula (not shown in FIG. 4), such that upon piercing the skin of the user with the needle 58, an end of the hollow cannula is guided through the skin of the user by the needle 58. Thereafter, the needle 58 may be removed, leaving the hollow cannula in place, with one end of the cannula located within the body of the user and the other end of the cannula in fluid flow connection with the fluidic medium within the reservoir 40, to convey pumped infusion media from the reservoir 40 to the body of the user.

Figure 5A:
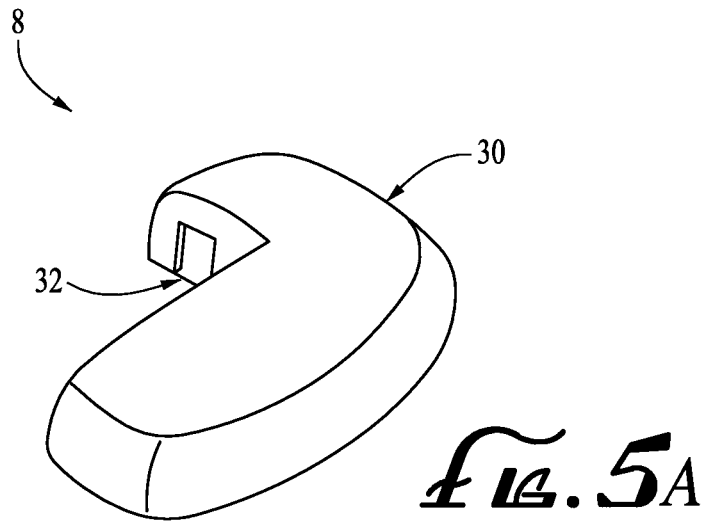
FIG. 5A illustrates a durable portion of a delivery device in accordance with an embodiment of the present invention.
Figure 5B:
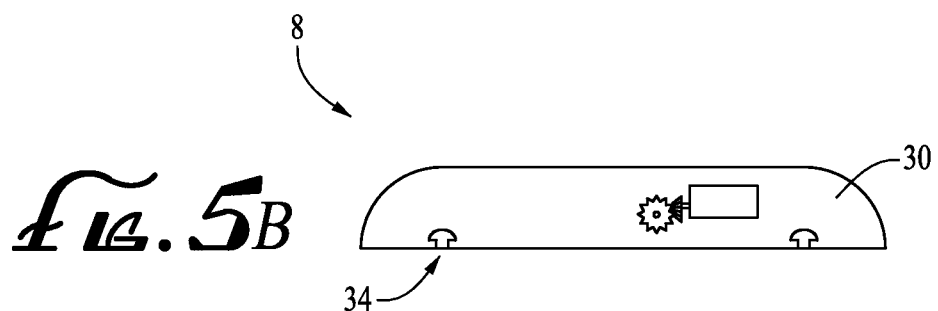
FIG. 5B illustrates a section view of a durable portion of a delivery device in accordance with an embodiment of the present invention.
Figure 5C:
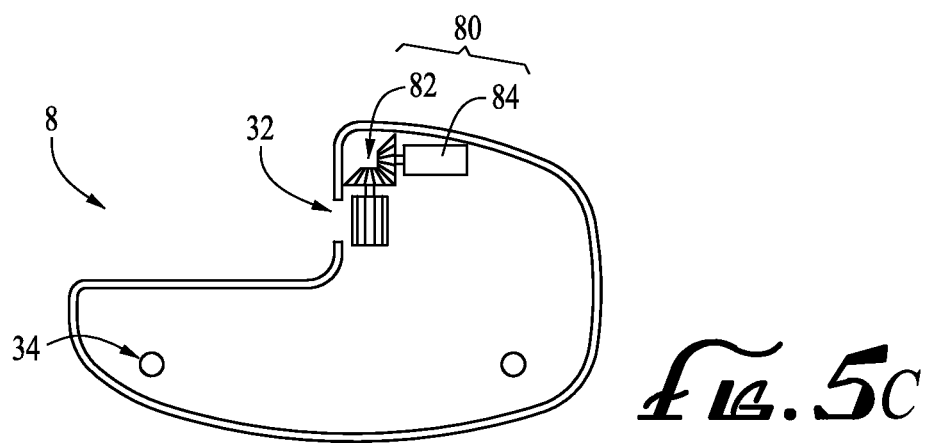
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82. In various embodiments, the durable housing 30 may include an interior volume for housing the motor 84, the drive device linkage portion 82, other electronic circuitry, and a power source (not shown in FIGS. 5A, 5B, and 5C). Also, in various embodiments, the durable housing 30 is configured with an opening 32 for receiving a plunger arm 60 (refer to FIG. 3). Also, in various embodiments, the durable housing 30 may include one or more connection members 34, such as tabs, insertion holes, or the like, for connecting with the base 21 of the disposable housing 20 (refer to FIG. 3).

Figure 6A:
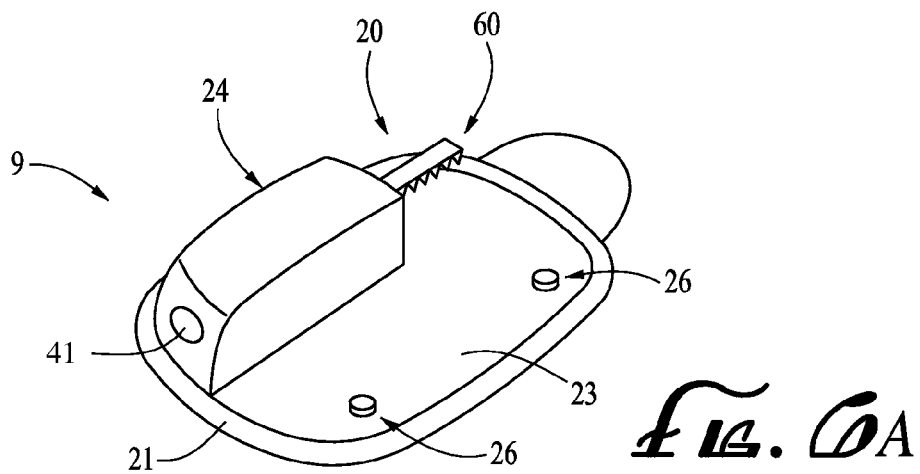
FIG. 6A illustrates a disposable portion of a delivery device in accordance with an embodiment of the present invention.
Figure 6B:
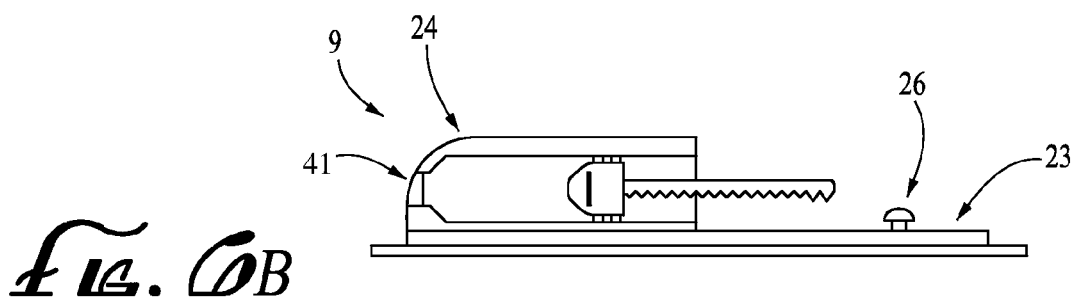
FIG. 6B illustrates a section view of a disposable portion of a delivery device in accordance with an embodiment of the present invention.
Figure 6C:
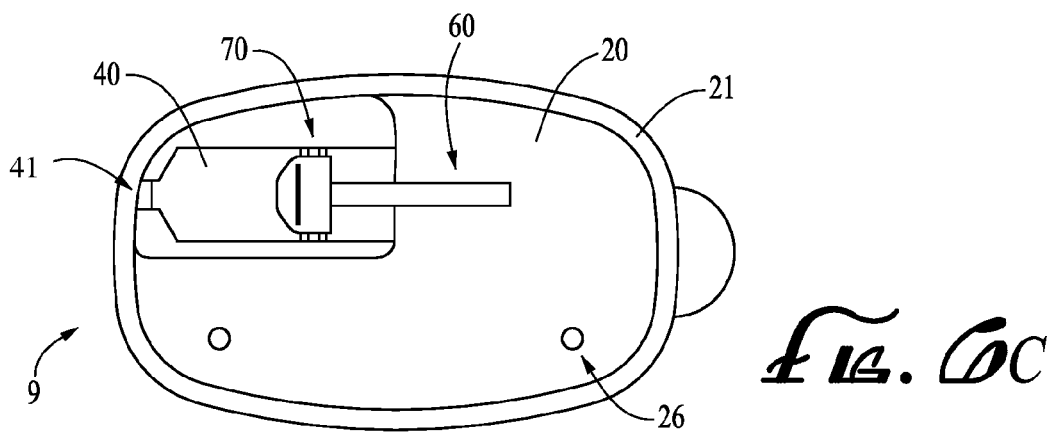
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir 40, the plunger arm 60, and a plunger head 70. In some embodiments, the disposable housing 20 includes the base 21 and the reservoir retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir 40 is housed within the reservoir retaining portion 24 of the disposable housing 20, and the reservoir 40 is configured to hold a fluidic medium. Also, in various embodiments, the plunger head 70 is disposed at least partially within the reservoir 40 and is moveable within the reservoir 40 to allow the fluidic medium to fill into the reservoir 40 and to force the fluidic medium out of the reservoir 40. In some embodiments, the plunger arm 60 is connected to or is connectable to the plunger head 70. Also, in some embodiments, a portion of the plunger arm 60 extends to outside of the reservoir retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir 40. When the interior volume of the reservoir 40 is filled with a fluidic medium and an infusion path is provided from the reservoir 40 to the body of a user, the plunger head 70 may be moved within the reservoir 40 to force the fluidic medium from the reservoir 40 and into the infusion path, so as to deliver the fluidic medium to the body of the user.

In various embodiments, once the reservoir 40 has been sufficiently emptied or otherwise requires replacement, a user may simply remove the durable housing 30 from the disposable housing 20, and replace the disposable portion 9, including the reservoir 40, with a new disposable portion having a new reservoir. The durable housing 30 may be connected to the new disposable housing of the new disposable portion, and the delivery device including the new disposable portion may be secured to the skin of a user, or otherwise attached to the user. In various other embodiments, rather than replacing the entire disposable portion 9 every time the reservoir 40 is emptied, the reservoir 40 may be refilled with a fluidic medium. In some embodiments, the reservoir 40 may be refilled while remaining within the reservoir retaining portion 24 (refer to FIG. 6B) of the disposable housing 20. Also, in various embodiments, the reservoir 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir 40 includes reservoir circuitry (not shown). In various embodiments, the reservoir circuitry stores information such as, but not limited to, at least one of (i) an identification string identifying the reservoir 40; (ii) a manufacturer of the reservoir 40; (iii) contents of the reservoir 40; and (iv) an amount of contents in the reservoir 40. In some embodiments, the delivery device 12 includes the reservoir status circuitry (not shown), and the reservoir status circuitry is configured to read data from the reservoir circuitry when the reservoir 40 is inserted into the disposable portion 9.

In various embodiments, the reservoir status circuitry is further configured to store data to the reservoir circuitry after at least some of the contents of the reservoir 40 have been transferred out of the reservoir 40, so as to update information in the reservoir circuitry related to an amount of contents still remaining in the reservoir 40. In some embodiments, the reservoir status circuitry is configured to store data to the reservoir circuitry, so as to update information in the reservoir circuitry related to an amount of contents still remaining in the reservoir 40, when the reservoir 40 is inserted into the disposable portion 9. In some embodiments, the delivery device 12 includes the reservoir status circuitry (not shown) and the reservoir 40 includes the reservoir circuitry (not shown), and the reservoir status circuitry selectively inhibits use of the delivery device 12 or selectively provides a warning signal based on information read by the reservoir status circuitry from the reservoir circuitry.

Figure 7A:
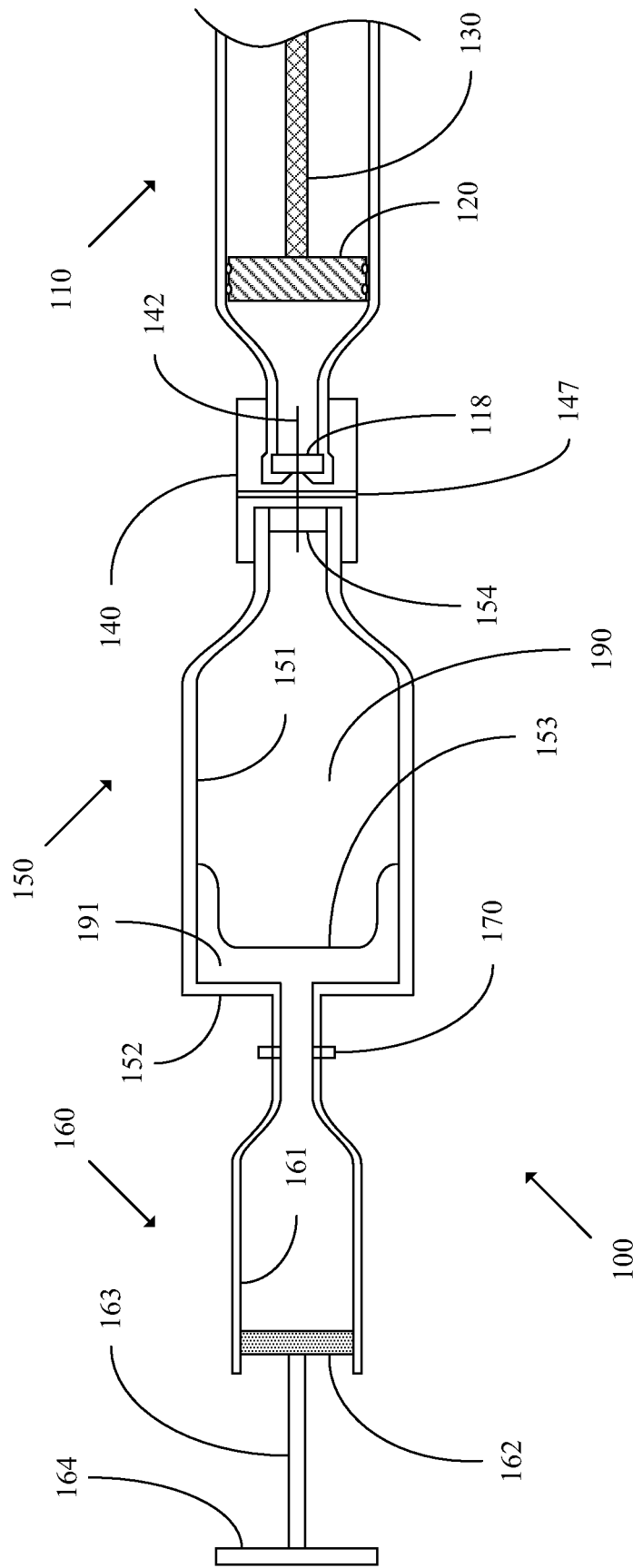
FIG. 7A illustrates a cross-sectional view of a system in accordance with an embodiment of the present invention.

FIG. 7A illustrates a cross-sectional view of a system 100 in accordance with an embodiment of the present invention. The system 100 includes a reservoir 110, a plunger head 120, a plunger arm 130, a transfer guard 140, a vial 150, and a pressure providing device 160. The reservoir 110 has a hollow interior for containing a fluidic medium. The plunger head 120 is located within the reservoir 110 and is moveable in an axial direction of the reservoir 110, to expand or contract an interior volume of the reservoir 110. The plunger arm 130 is connected to the plunger head 120. In various embodiments, the reservoir 110 includes a septum 118 that is able to be pierced by a needle, such that the hollow interior of the reservoir 110 is able to be filled with a fluidic medium that passes through the needle once the needle has pierced the septum 118.

The vial 150 includes a diaphragm 153 that is connected to an inner surface 151 of the vial 150. The inner surface 151 of the vial 150 and an outer surface of the diaphragm 153 define a fillable volume 190 of the vial 150 that is able to contain a fluidic medium. In various embodiments, the diaphragm 153 comprises rubber, plastic, or the like, and is flexible. In some embodiments, the vial 150 further includes a septum 154 that is able to be pierced by a needle, such that a fluidic medium is able to be expelled from the vial 150 through the needle once the needle has pierced the septum 154.

In various embodiments, the vial 150 includes a bottom surface 152 with an opening for allowing air or other motivation to enter into a pressurizable volume 191 of the vial 150 on an opposite side of the diaphragm 153 from a side of the diaphragm 153 that is in contact with the fluidic medium in the vial 150. The diaphragm 153 separates the fillable volume 190 of the vial 150 from the pressurizable volume 191 of the vial 150. The diaphragm 153 is inflatable to reduce the fillable volume 190 in a case where a pressure within the pressurizable volume 191 is increased. In various embodiments, the diaphragm 153 is deflatable to increase the fillable volume 190 in a case where the pressure within the pressurizable volume 191 is decreased.

The transfer guard 140 includes one or more needles 142 for providing a fluid path from an interior volume of the vial 150 to an interior volume of the reservoir 110. In various embodiments, the transfer guard 140 includes walls that help to shield the one or more needles 142 from contact with a hand of a user when the user is connecting the vial 150 and the reservoir 110 with the transfer guard 140. The one or more needles 142 of the transfer guard 140 are able to pierce the septum 154 of the vial 150 and the septum 118 of the reservoir 110, so as to provide a fluid path from the vial 150 to the reservoir 110. In various embodiments, a membrane 147 is incorporated into the fluid flow path in the transfer guard 140 to trap air bubbles as a fluidic medium passes along the fluid flow path from the vial 150 to the reservoir 110.

The pressure providing device 160 may include, for example, a syringe, or the like, for forcing air or other motivation, such as a fluid, through the opening in the bottom surface 152 of the vial 150 and into the pressurizable volume 191. In various other embodiments, the pressure providing device 160 may include, for example, a pump, or the like for providing pressure. The pressure providing device 160 is connected to the vial 150 at a connection point 170 by, for example, an air tight connector, a screw connection, a clamp, or the like. In various embodiments, the pressure providing device 160 allows for changing a pressure within the pressurizable volume 191.

In FIG. 7A, the pressure providing device 160 is illustrated as a syringe having an inner surface 161 defining a hollow interior, a plunger head 162, a plunger arm 163 connected to the plunger head 162, and a handle 164 connected to the plunger arm 163. The syringe is configured such that air or other motivation is expelled from the syringe when the handle 164 is pressed to cause the plunger head 162 to advance within the interior of the syringe. In various embodiments, the syringe is connectable to the vial 150 such that in a case where the syringe is filled with air and is connected to the vial 150 and the plunger head 162 within the syringe is advanced, a pressure within the pressurizable volume 191 is increased so as to cause the diaphragm 153 to inflate and reduce the fillable volume 190.

In some embodiments, the diaphragm 153 is deflatable to evacuate air from an interior volume of the reservoir 110 into the fillable volume 190 of the vial 150 in a case where the interior volume of the reservoir 110 and the fillable volume 190 of the vial 150 are connected by the one or more needles 142 and a vacuum is applied to the pressurizable volume 191 of the vial. Also, in some embodiments, the diaphragm 153 is inflatable to force a fluidic medium out of the fillable volume 190 of the vial 150 and into the interior volume of the reservoir 110 in a case where the fillable volume 190 of the vial 150 is holding the fluidic medium and the fillable volume 190 of the vial 150 is connected to the interior volume of the reservoir 110 by the one or more needles 142 and the pressure within the pressurizable volume 191 is increased.

A method in accordance with an embodiment of the present invention allows for filling the reservoir 110 in the system 100. The method includes connecting the pressure providing device 160 to one end of the vial 150 and connecting another end of the vial 150 to the reservoir 110 using the transfer guard 140. An example of such a connected structure is illustrated in FIG. 7A. The method further includes using the pressure providing device 160 to apply pressure to a side of the diaphragm 153 in the vial 150 that is opposite a side of diaphragm 153 that is in contact with a fluidic medium. For example, in a case that the pressure providing device 160 includes a syringe, the handle 164 is pressed so as to advance the plunger head 162 within the syringe and expel air or other motivation into the pressurizable volume 191 of the vial 150 to thereby apply pressure to the diaphragm 153.

Figure 7B:
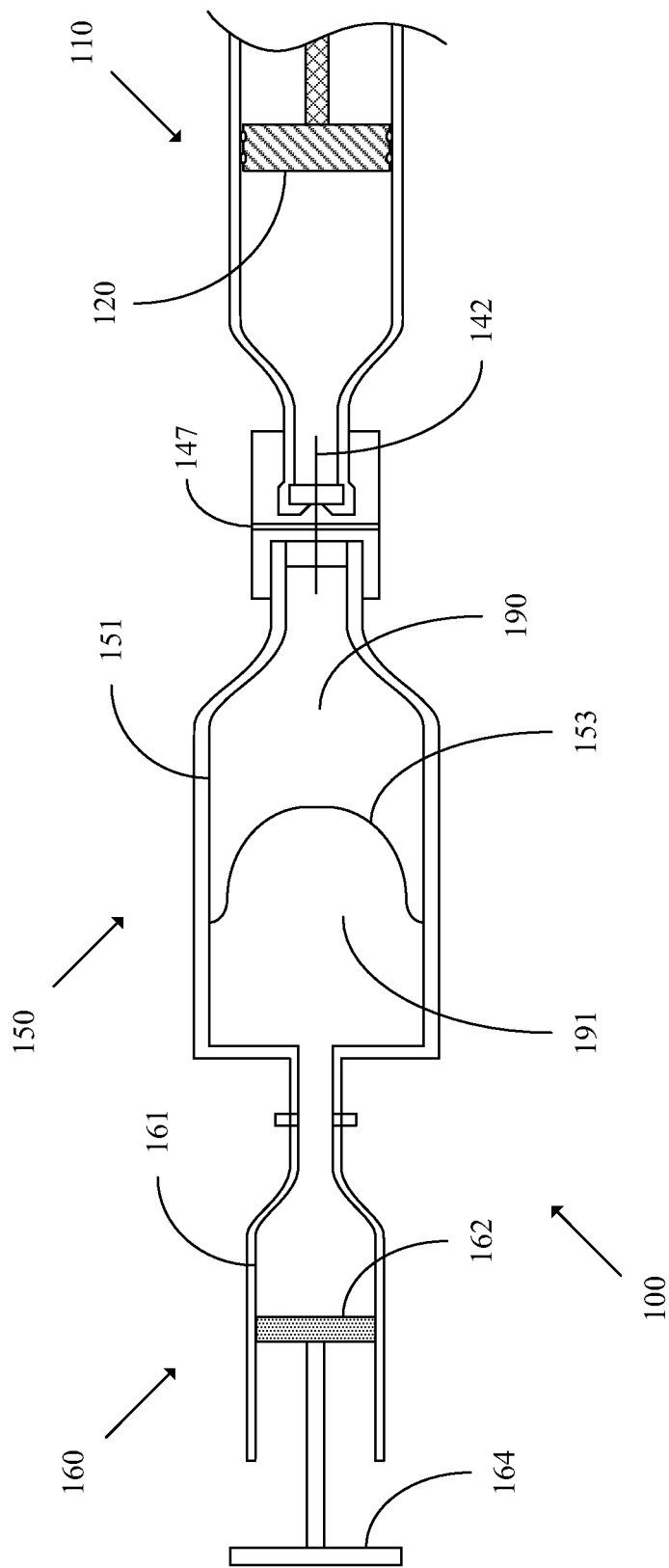
FIG. 7B illustrates a cross-sectional view of a system in accordance with an embodiment of the present invention.

The diaphragm 153 within the vial 150 is flexible, so the diaphragm 153 expands into the fillable volume 190 when a pressure is applied to the diaphragm 153 by the pressure providing device 160. FIG. 7B illustrates a case in which the plunger head 162 of the pressure providing device 160 has been advanced so as to increase a pressure of a side of the diaphragm 153 in the vial 150 and, thus, cause the diaphragm 153 to expand within the vial 150. As the diaphragm 153 expands due to the pressure from the pressure providing device 160, the fillable volume 190 of the vial 150 in which the fluidic medium is contained is reduced in size and, as a consequence, the fluidic medium is forced out of the vial 150 through the fluid path to the interior volume of the reservoir 110. The inflow of fluidic medium to the interior volume of the reservoir 110 causes the plunger head 120 to move backwards within the reservoir 110. Increasing pressure may be applied from the pressure providing device 160 to the diaphragm 153 of the vial 150 until a desired amount of fluidic medium has been filled into the reservoir 110.

Thus, embodiments of the present invention provide a flexible diaphragm in a bottom of a vial and allow for external pressure to be applied to the flexible diaphragm so as to force a fluidic medium, such as insulin, or the like, into a reservoir. In various embodiments, the membrane 147 is incorporated into the fluid flow path to trap air bubbles in a fluidic medium. In some embodiments of the method using the system 100, an initial vacuum is applied to the vial 150 to evacuate air in a dead space of the reservoir 110 into the vial 150 prior to filling the reservoir 110.

Figure 8:
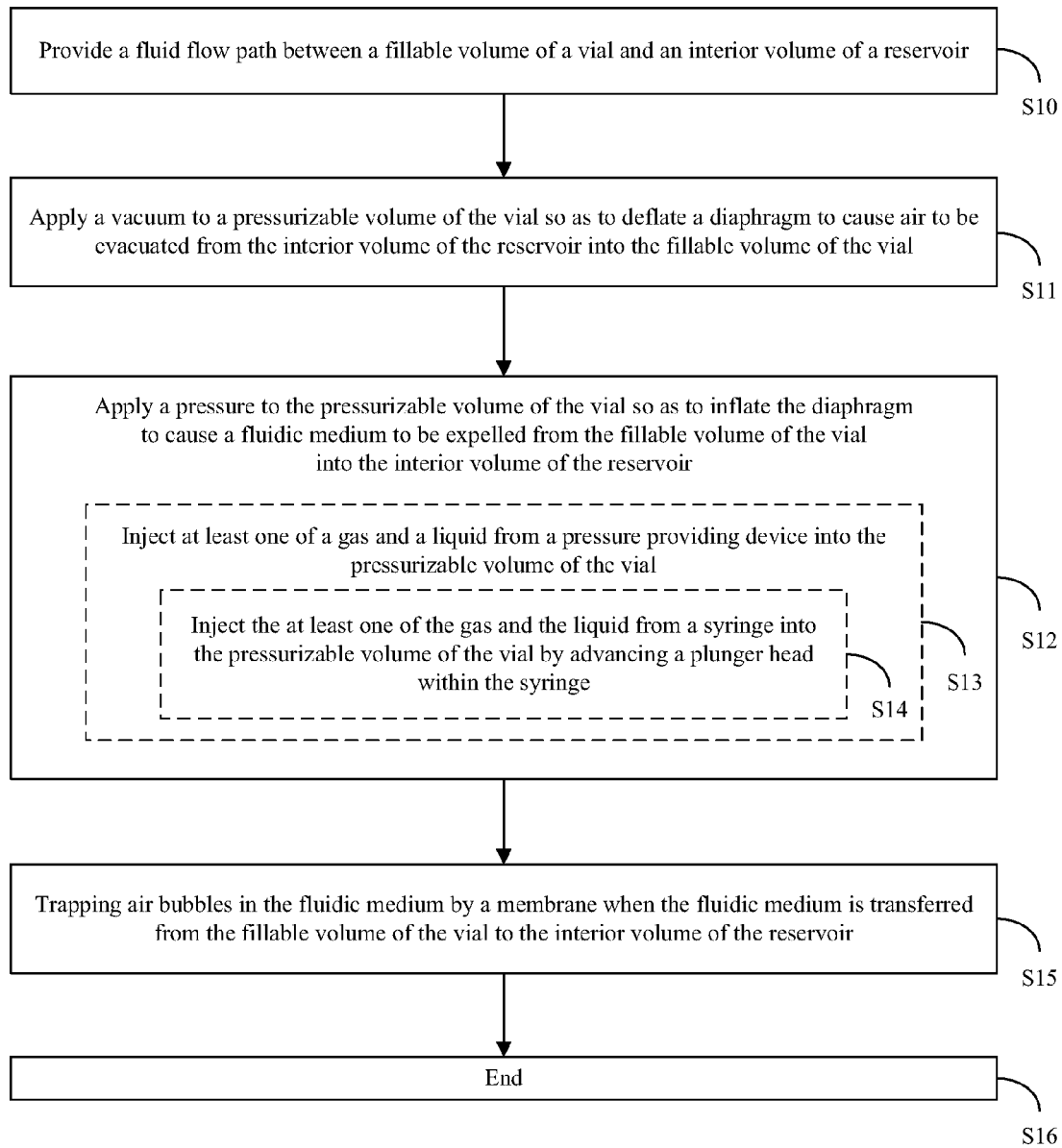
FIG. 8 illustrates a flowchart for a method in accordance with an embodiment of the present invention.

FIG. 8 illustrates a flowchart of a method in accordance with an embodiment of the present invention. In S10, a fluid flow path is provided between a fillable volume of a vial and an interior volume of a reservoir, and the method continues to S11. In S11, a vacuum is applied to a pressurizable volume of the vial so as to deflate a diaphragm to cause air to be evacuated from the interior volume of the reservoir into the fillable volume of the vial, and the method continues to S12. In S12, a pressure is applied to the pressurizable volume of the vial so as to inflate the diaphragm to cause a fluidic medium to be expelled from the fillable volume of the vial into the interior volume of the reservoir, and the method continues to S15.

In various embodiments, S12 includes S13 in which at least one of a gas and a liquid in injected from a pressure providing device into the pressurizable volume of the vial. Also, in various embodiments, S13 includes S14 in which the at least one of the gas and the liquid is injected from a syringe into the pressurizable volume of the vial by advancing a plunger head within the syringe. In S15, air bubbles are trapped in the fluidic medium by a membrane when the fluidic medium is transferred from the fillable volume of the vial to the interior volume of the reservoir, and the method then ends in S16.

Figure 9A:
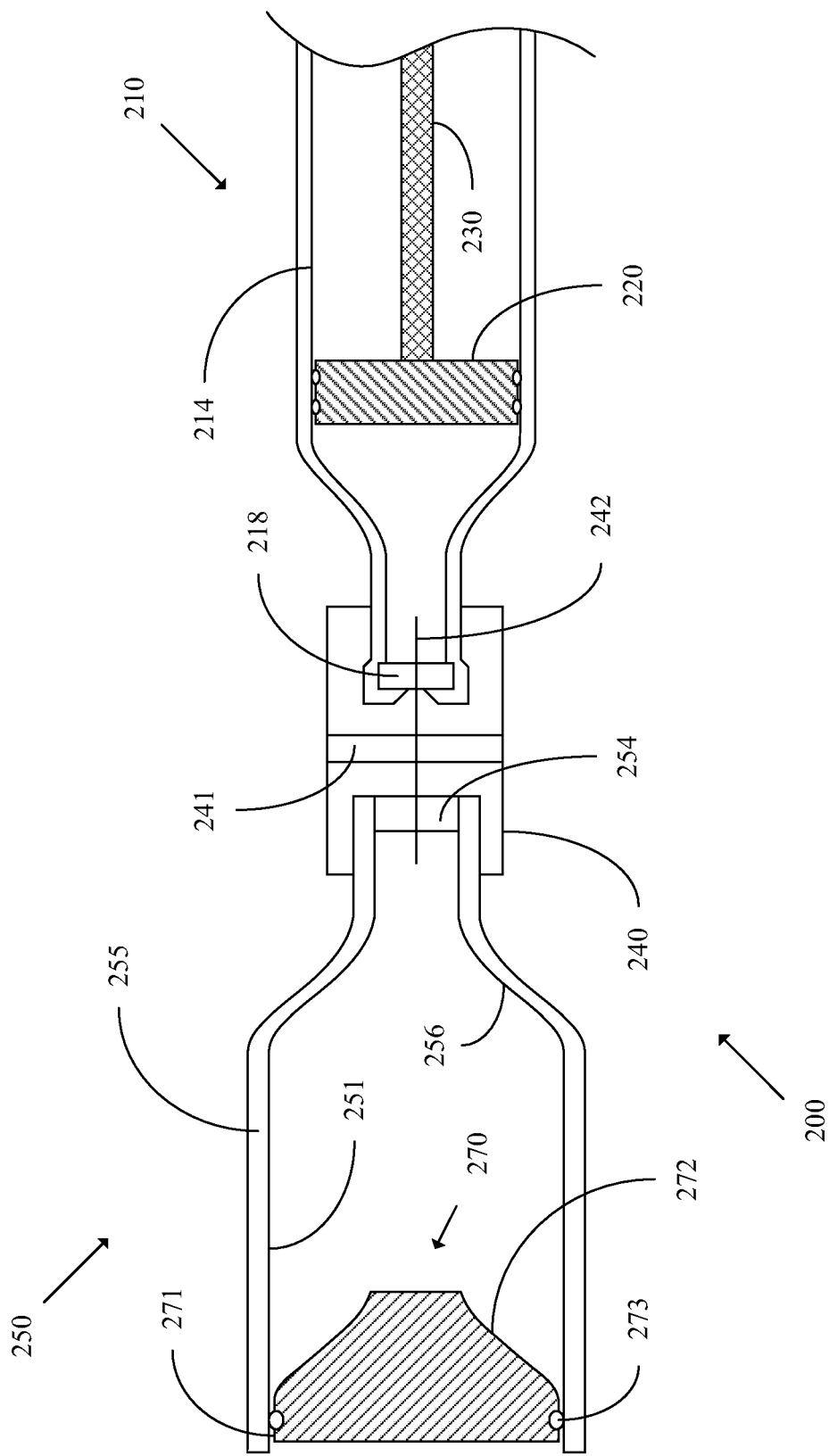
FIG. 9A illustrates a cross-sectional view of a system in accordance with an embodiment of the present invention.

FIG. 9A illustrates a cross-sectional view of a system 200 in accordance with an embodiment of the present invention. The system 200 includes a reservoir 210, a plunger head 220, a plunger arm 230, a transfer guard 240, a vial 250, and a moveable element 270. The reservoir 210 has a hollow interior for containing a fluidic medium. The plunger head 220 is located within the reservoir 210 and is moveable in an axial direction of the reservoir 210, to expand or contract an interior volume of the reservoir 210. The plunger arm 230 is connected to the plunger head 220. In various embodiments, the reservoir 210 includes a septum 218 that is able to be pierced by a needle, such that the hollow interior of the reservoir 210 is able to be filled with a fluidic medium that passes through the needle once the needle has pierced the septum 218.

The moveable element 270 is located within the vial 250 and is moveable within the vial 250 to expand or contract an interior volume of the vial 250. An inner surface 251 of the vial 250 and a surface of the moveable element 270 define an interior volume of the vial 250 that is able to contain a fluidic medium. In various embodiments, the moveable element 270 comprises rubber, plastic, or the like. Also, in various embodiments, the moveable element 270 comprises a plunger, or the like. In some embodiments, the vial 250 further includes a septum 254 that is able to be pierced by a needle, such that a fluidic medium is able to be expelled from the vial 250 through the needle once the needle has pierced the septum 254.

The moveable element 270 is able to move within the vial 250 when a pressure is applied to the moveable element 270. In various embodiments, the moveable element includes a barrel portion 271 and a curved portion 272, where a contour of an outer surface of the barrel portion 271 is substantially the same as a contour of the inner surface 251 of a barrel portion 255 of the vial 250, and where a contour of an outer surface of the curved portion 272 is substantially the same as a contour of a curved portion 256 of the vial 250. Also, in various embodiments, the moveable element 270 includes one or more seals 273, such as o-rings or the like, that surround the barrel portion 271 of the moveable element 270 and that are in contact with the inner surface 251 of the barrel portion 255 of the vial 250 when the moveable element 270 is within the vial 250. The moveable element 270 is advanceable within the vial 250 to reduce the interior volume of the vial 250. Also, in various embodiments, the moveable element 270 is retractable within the vial 250 to increase the interior volume of the vial 250.

The transfer guard 240 includes one or more needles 242 for providing a fluid path from an interior volume of the vial 250 to an interior volume of the reservoir 210. In various embodiments, the transfer guard 240 includes walls that help to shield the one or more needles 242 from contact with a hand of a user when the user is connecting the vial 250 and the reservoir 210 with the transfer guard 240. The one or more needles 242 of the transfer guard 240 are able to pierce the septum 254 of the vial 250 and the septum 218 of the reservoir 210, so as to provide a fluid path from the vial 250 to the reservoir 210. In various embodiments, the transfer guard 240 may include a membrane 241 that is incorporated into the fluid flow path of the transfer guard 240 to trap air bubbles as a fluidic medium passes along the fluid flow path from the vial 250 to the reservoir 210.

A method in accordance with an embodiment of the present invention allows for filling the reservoir 210 in the system 200. The method includes connecting the vial 250 to the reservoir 210 using the transfer guard 240. An example of such a connected structure is illustrated in FIG. 9A. The method further includes applying pressure to a side of the moveable element 270 in the vial 250 that is opposite a side of moveable element 270 that is in contact with a fluidic medium. For example, a user or a device may press on an external surface of the moveable element 270 to advance the moveable element 270 within the vial 250. Thus, the moveable element 270 acts as a moveable bottom of the vial 250. In various embodiments, the moveable element 270 may further include a handle (not shown) connected to the moveable element 270 for applying pressure to the moveable element 270.

Figure 9B:
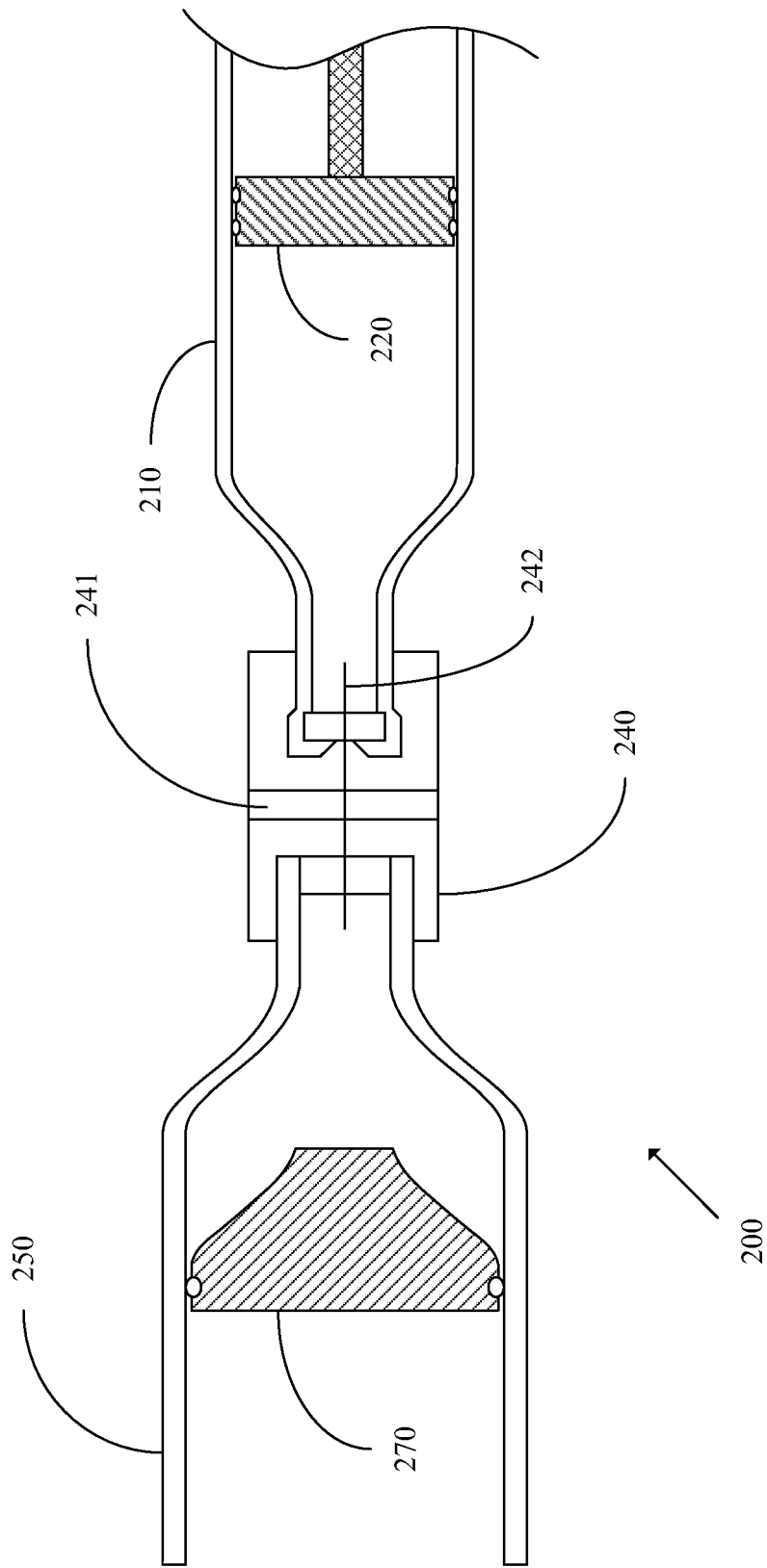
FIG. 9B illustrates a cross-sectional view of a system in accordance with an embodiment of the present invention.

When a pressure is applied to the moveable element 270 to advance the moveable element 270 within the vial 250, the fluidic medium within the vial 250 is forced through the one or more needles 242 and into the reservoir 210. FIG. 9B illustrates a cross-sectional view of the system 200 once the moveable element 270 has been at least partially advanced within the vial 250. When a force is applied to the moveable element 270 to force fluidic medium from the vial 250 to fill the reservoir 210, the plunger head 220 is forced backward within the reservoir 210 by the force of the fluidic medium entering the reservoir 210. Thus, embodiments of the present invention allow for a storage vial with a moveable bottom, and for applying a pressure to the moveable bottom of the storage vial to fill a reservoir. Also, when the fluidic medium passes from the vial 250 to the reservoir 210, the fluidic medium is passed through the membrane 241 of the transfer guard 240, which substantially removes air bubbles from the fluidic medium prior to the fluidic medium filling into the reservoir 210.

Figure 10:
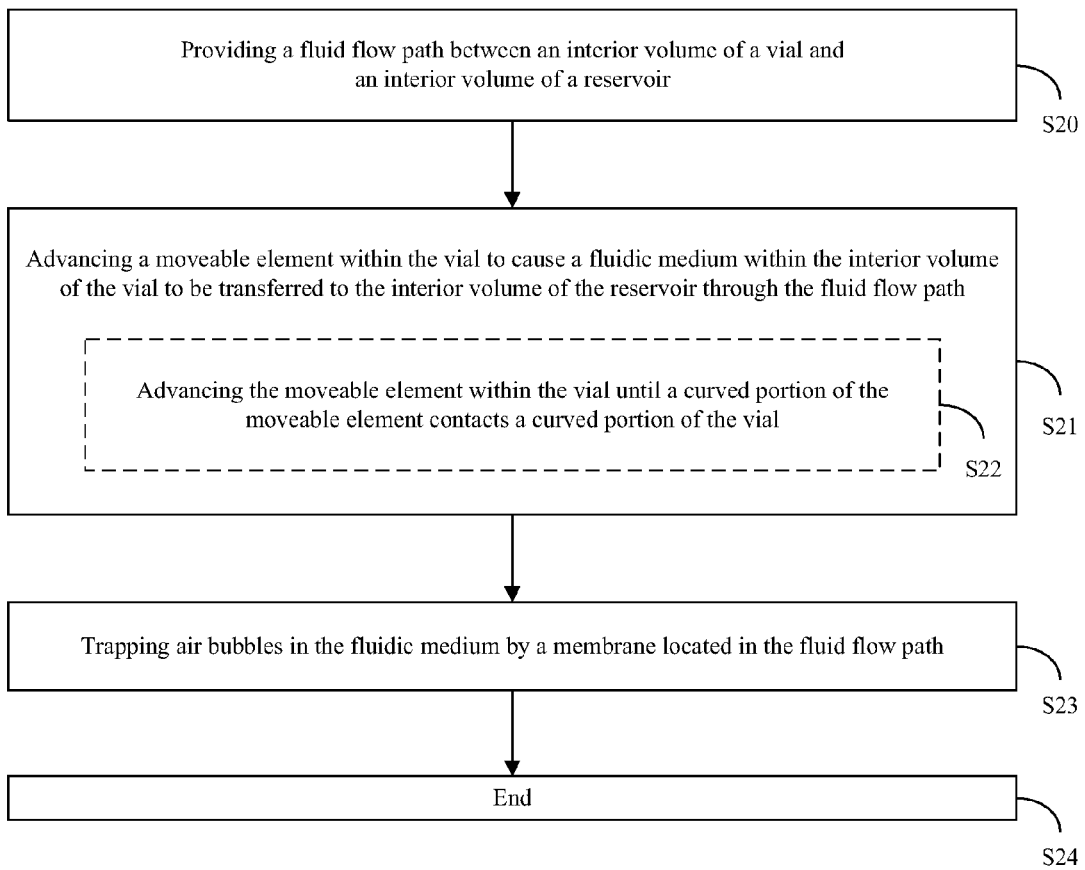
FIG. 10 illustrates a flowchart for a method in accordance with an embodiment of the present invention.

FIG. 10 illustrates a flowchart of a method in accordance with an embodiment of the present invention. In S20, a fluid flow path is provided between an interior volume of a vial and an interior volume of a reservoir, and the method continues to S21. In S21, a moveable element is advanced within the vial to cause a fluidic medium within the interior volume of the vial to be transferred to the interior volume of the reservoir through the fluid flow path, and the method continues to S23. In various embodiments, S21 includes S22 in which the moveable element is advanced within the vial until a curved portion of the moveable element contacts a curved portion of the vial. In S23, air bubbles are trapped in the fluidic medium by a membrane located in the fluid flow path, and the method then ends in S24.

Figure 11A:
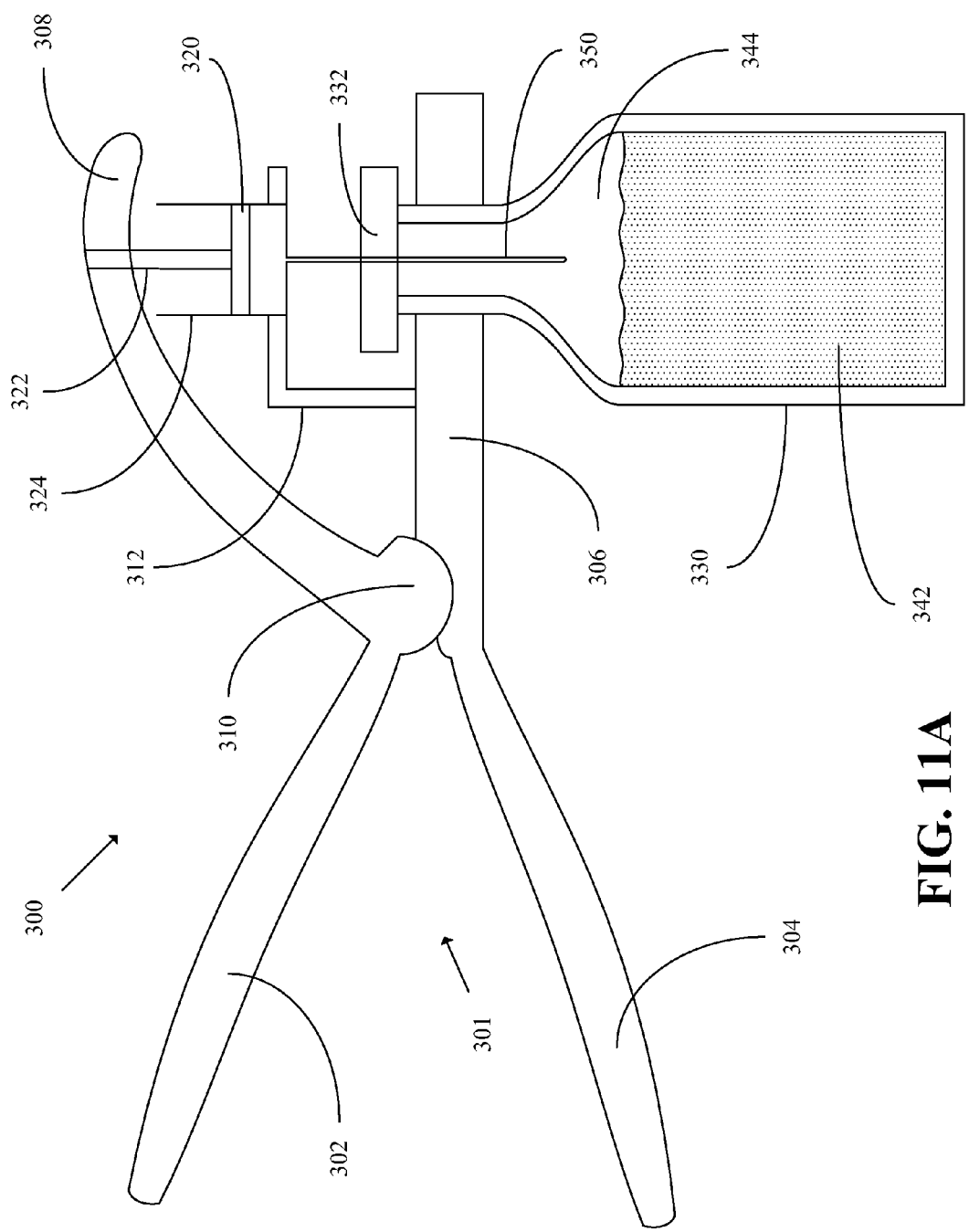
FIG. 11A illustrates a cross-sectional view of a system in accordance with an embodiment of the present invention.

FIG. 11A illustrates a cross-sectional view of a system 300 in accordance with an embodiment of the present invention. The system 300 includes a degassing tool 301 and a vial 330. The degassing tool 301 includes a first handle 302, a second handle 304, a pivot member 310, a first arm 308, a second arm 306, a holding arm 312, a plunger housing 324, a plunger head 320, a plunger arm 322, and an insertion member 350. The vial 330 contains a fluidic medium, such as insulin, or the like, up to a certain level within the vial 330, and an area of the vial 330 above the fluidic medium forms a headspace 344 of the vial 330. The vial includes a septum 332 that may be pierced by the insertion member 350 of the degassing tool 301.

The first handle 302, the second handle 304, the first arm 308, and the second arm 306 are connected together by the pivot member 310. In various embodiments, the first handle 302, the pivot member 310, and the first arm 308 are formed as a single unit, and the second handle 304 and the second arm 306 are formed as a single unit. The first handle 302 is able to pivot toward and away from the second handle 304. The second arm 306 may have a cavity for surrounding a neck of a vial. The holding arm 312 extends from the second arm 306 and holds the plunger housing 324 between the first arm 308 and the second arm 306. The plunger head 320 is connected to the plunger arm 322 and the plunger head 320 is able to slide within the plunger housing 324. The insertion member 350 may be, for example, a needle, and is connected to an output port of the plunger housing 324. The plunger arm 322 is connected to the first arm 308.

The degassing tool 301 is configured such that when the first handle 302 is pivoted away from the second handle 304, the first arm 308 is pivoted such that the plunger arm 322 causes the plunger head 320 to advance within the plunger housing 324 to reduce a volume in the plunger housing 324 between the plunger head 320 and the output port to the insertion member 350. The degassing tool 301 is also configured such that when the first handle 302 is pivoted toward the second handle 304, the first arm 308 is pivoted such that the plunger arm 322 causes the plunger head 320 to retract within the plunger housing 324 to increase a volume in the plunger housing 324 between the plunger head 320 and the output port to the insertion member 350.

A method in accordance with the present invention allows for degassing the vial 330 using the degassing tool 301. In a step of the method, the first handle 302 of the degassing tool 301 is pivoted away from the second handle 304, which causes the first arm 308 to push on the plunger arm 322 and, thus, advance the plunger head 320 within the plunger housing 324. In another step of the method, the insertion member 350 is inserted through the septum 332 of the vial 330 and into the headspace 344 of the vial 330 above the fluidic medium 342 within the vial 330. An example of such a connection of the degassing tool 301 and the vial 330 is illustrated in FIG. 11A.

Figure 11B:
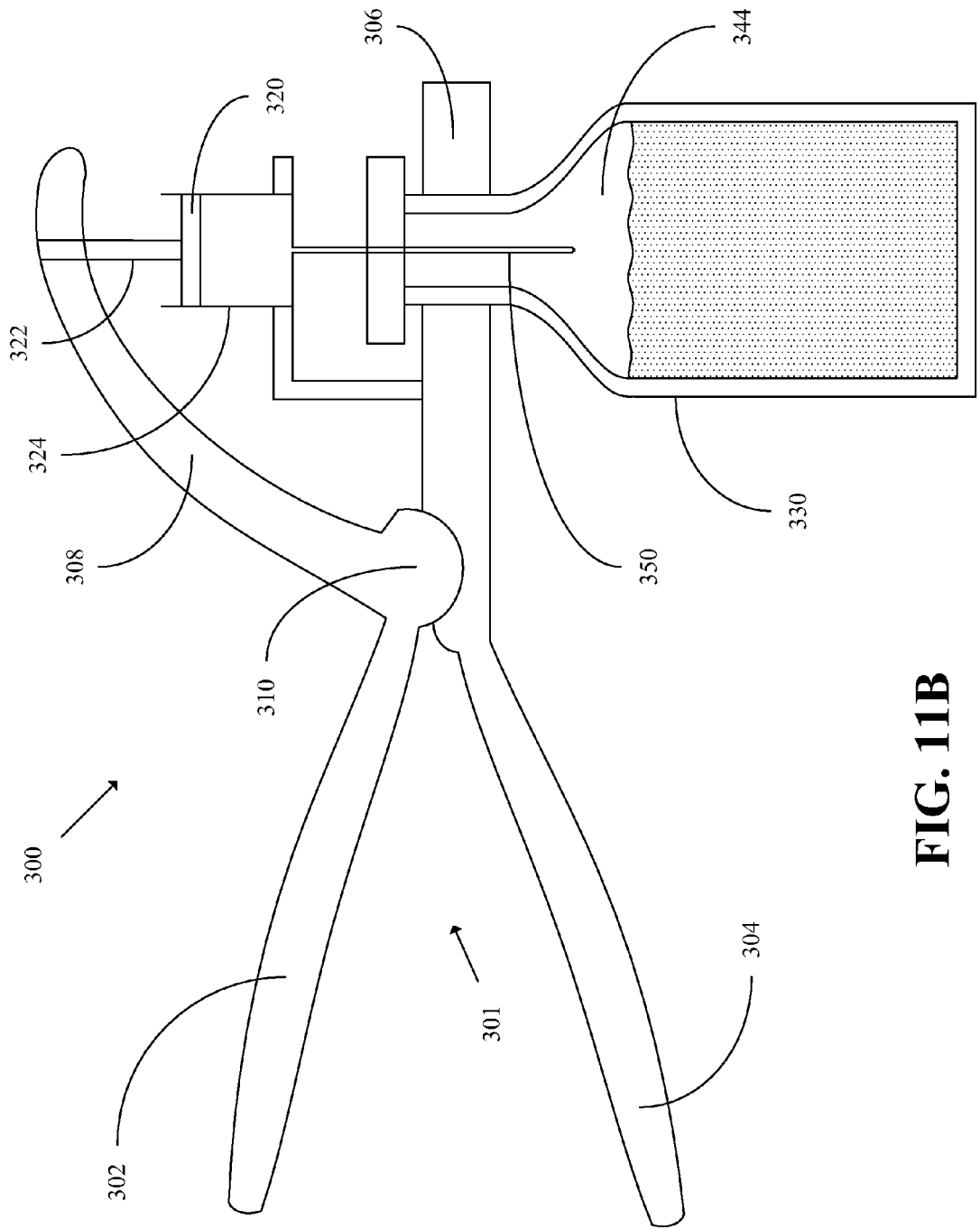
FIG. 11B illustrates a cross-sectional view of a system in accordance with an embodiment of the present invention.

In yet another step of the method, the first handle 302 of the degassing tool 301 is pivoted toward the second handle 304, which causes the first arm 308 to pull on the plunger arm 322 and, thus, retract the plunger head 320 within the plunger housing 324. FIG. 11B illustrates a cross-section of the system 300 in accordance with an embodiment of the present invention when the first handle 302 has been pivoted toward the second handle 304. When the plunger head 320 retracts within the plunger housing 324, air or gas in the headspace 344 of the vial 330 is drawn through the insertion member 350 and into the plunger housing 324. In various embodiments, the degassing tool 301 is operated by a hand of a user. Once the gas has been drawn out of the headspace 344 of the vial 330, the vial 330 is disconnected from the degassing tool 301 and may be used to fill a reservoir. Thus, embodiments of the present invention provide for a hand powered purging device or degassing tool that can be connected to existing drug vials and, by performing a pumping action, can reduce a pressure inside of a vial by causing out-gassing to occur before using the vial to fill a reservoir.

Figure 12:
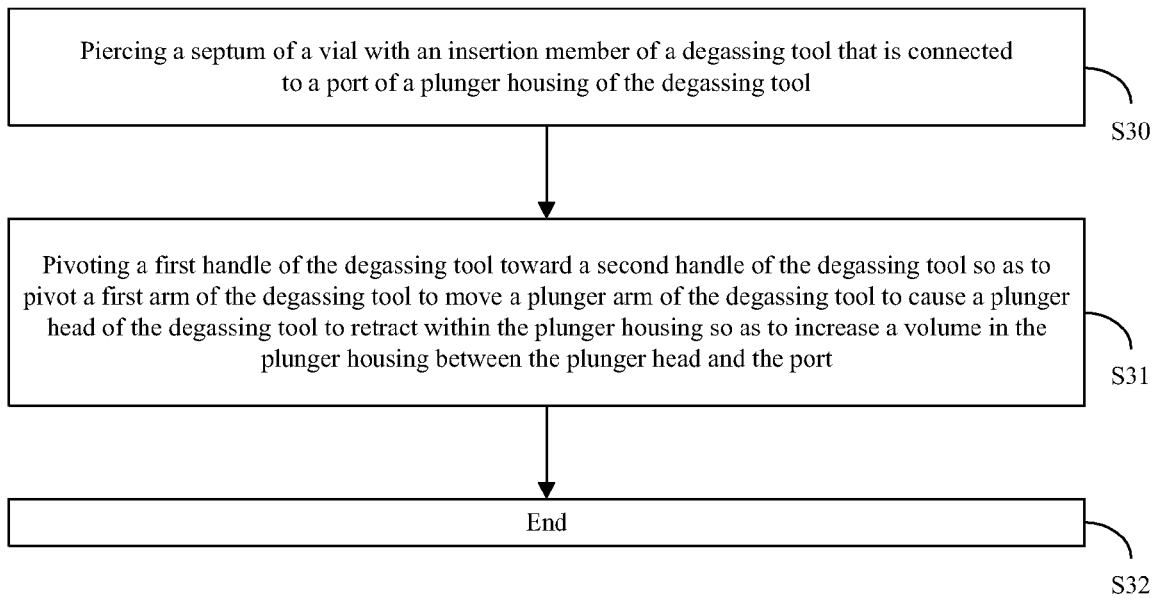
FIG. 12 illustrates a flowchart for a method in accordance with an embodiment of the present invention.

FIG. 12 illustrates a flowchart of a method in accordance with an embodiment of the present invention. In S30, a septum of a vial is pierced with an insertion member of a degassing tool that is connected to a port of a plunger housing of the degassing tool, and the method continues to S31. In S31, a first handle of the degassing tool is pivoted toward a second handle of the degassing tool so as to pivot a first arm of the degassing tool to move a plunger arm of the degassing tool to cause a plunger head of the degassing tool to retract within the plunger housing so as to increase a volume in the plunger housing between the plunger head and the port. Gas is extracted from the vial and into the plunger housing through the insertion member when the volume in the plunger housing between the plunger head and the port is increased. The method then ends in S32.

Figure 13:
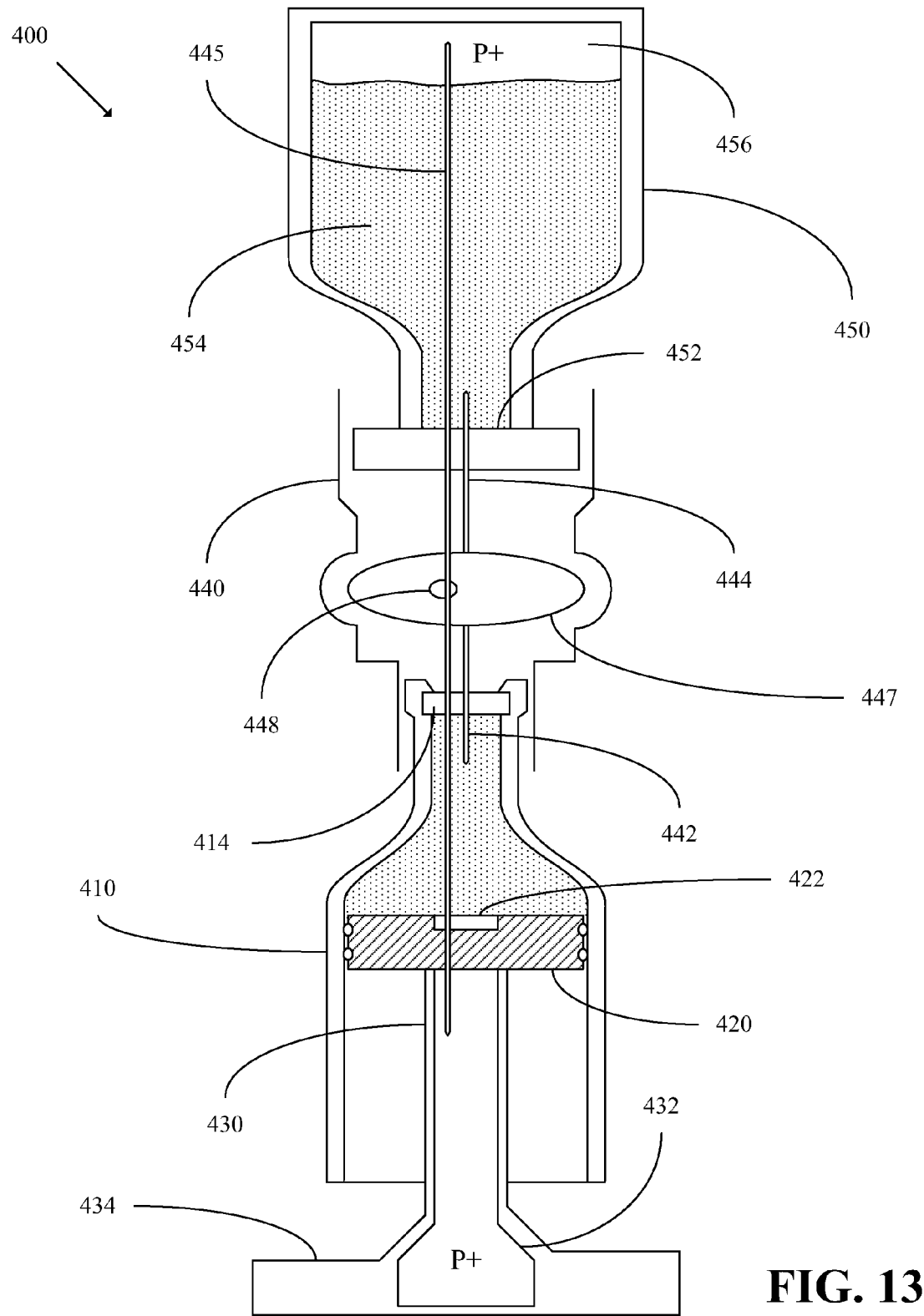
FIG. 13 illustrates a cross-sectional view of a system in accordance with an embodiment of the present invention.

FIG. 13 illustrates a cross-sectional view of a system 400 in accordance with an embodiment of the present invention. The system 400 includes a reservoir 410, a plunger head 420, a plunger head septum 422, a plunger rod 430, a handle 434, a pressurized vessel 432, a reservoir septum 414, a first short needle 442, a second short needle 444, an air filter 447, a hydrophobic membrane 448, a transfer guard 440, a vial 450, a vial septum 452, and a long needle 445. The vial 450 has a headspace 456 that is above a fluidic medium 454 within the vial 450.

The pressurized vessel 432 contains air under pressure and is located within the plunger rod 430 and the handle 434. The long needle 445 penetrates the plunger head septum 422, the reservoir septum 414, and the vial septum 452 to provide an air path between the pressurized vessel 432 and the headspace 456 in the vial 450. The hydrophobic membrane 448 restricts fluid and vapor from passing through the long needle 445. The first short needle 442, the filter 447, and the second short needle 444 provide a fluid path from the vial 450 to the reservoir 410. Thus, air passes through the long needle 445 from the pressurized vessel 432 to the headspace 456 in the vial 450, and the fluidic medium 454 in the vial 450 is forced out of the vial 450 due to the pressure from the pressurized vessel 432, and the fluidic medium 454 flows from the vial 450 through the second short needle 444, the filter 447, and the first short needle 442 to the reservoir 410. The filter 447 allows for filtering air bubbles from the fluidic medium as the fluidic medium passes from the vial 450 to the reservoir 410. In various embodiments, the pressurized vessel 432 is contained entirely within the plunger rod 430.

Figure 14:
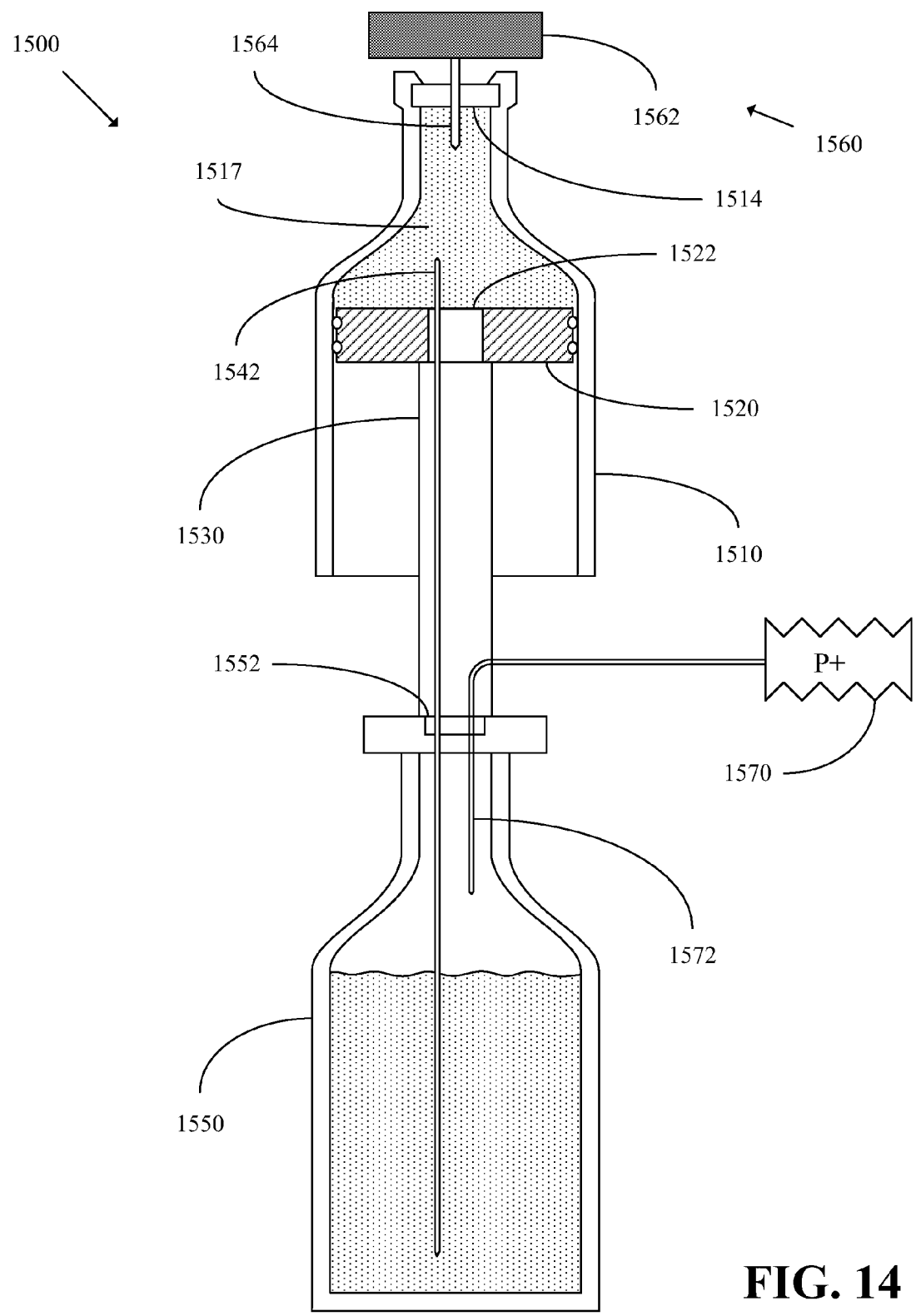
FIG. 14 illustrates a cross-sectional view of a system in accordance with an embodiment of the present invention.

FIG. 14 illustrates a cross-sectional view of a system 1500 in accordance with an embodiment of the present invention. The system 1500 includes a reservoir 1510, a plunger head 1520, a plunger head septum 1522, a reservoir septum 1514, a short needle 1564, a hydrophobic filter 1562, a plunger arm 1530, a vial 1550, a vial septum 1552, a bellows 1570, a needle 1572, and a long needle 1542. The reservoir 1510 has an interior volume 1517 for holding a fluidic medium between the plunger head 1520 and the septum 1514. The plunger head 1520 is moveable within the reservoir 1510. One end of the short needle 1564 is inserted through the reservoir septum 1514, and another end of the short needle 1564 is connected to the hydrophobic membrane 1562.

The vial 1550 is able to remain upright during a filling processes when a fluidic medium is transferred from the vial 1550 to the reservoir 1510. One end of the needle 1572 is connected to the bellows 1570, and another end of the needle 1572 pierces the vial septum 1552 and is positioned in a headspace within the vial 1550. The long needle 1542 is positioned to run from a lower region of the vial 1550 through the vial septum 1552 and through the plunger arm 1530, and through the plunger head septum 1522 into the interior volume 1517 of the reservoir 1510. In various embodiments, the plunger head septum 1522 may be at an end of a channel through a center of the plunger head 1520. Thus, the long needle 1542 is able to pass from a backside of the plunger head 1520 and into the interior volume 1517 of the reservoir 1510. The short needle 1564 allows for venting air through the hydrophobic membrane 1562, and the hydrophobic membrane 1562 substantially prevents a loss of a fluidic medium through the short needle 1564 during a filling process.

During a filling process, the bellows 1570 is compressed to force air through the needle 1572 and into the vial 1550. An increase pressure in the vial 1550 due to the air from the bellows 1570 forces a fluidic medium from the vial 1550 up the long needle 1542 and into the interior volume 1517 of the reservoir 1510. In various embodiments, during the filling processes, the plunger head 1520 is held stationary, but the reservoir 1510 is allowed to move upward with respect to the plunger head 1520 so as to increase a volume of the interior volume 1517 and allow for a fluidic medium to flow into the interior volume 1517 from the vial 1550 when the bellows 1570 is compressed.

Figure 15A:
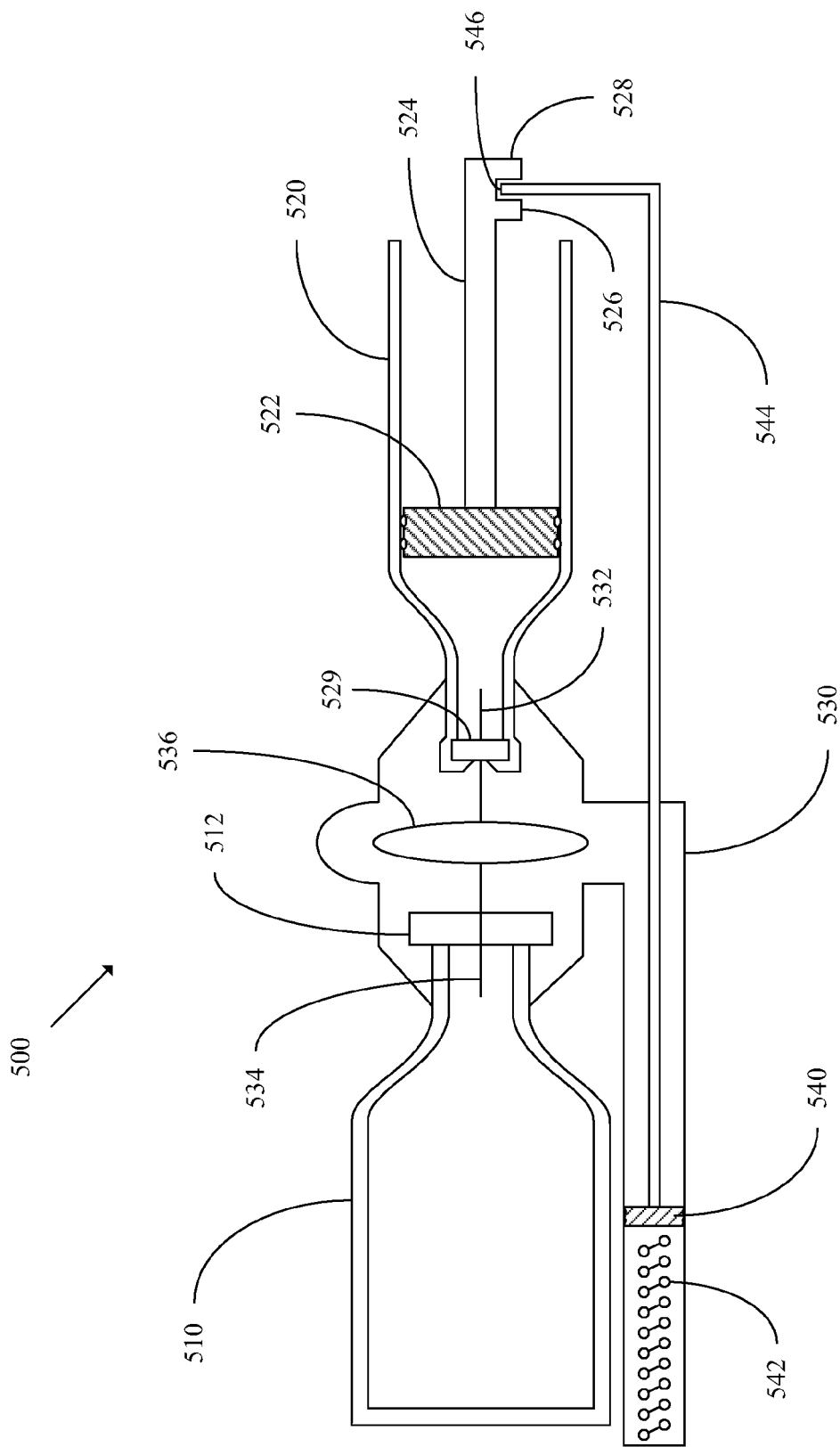
FIG. 15A illustrates a cross-sectional view of a system in accordance with an embodiment of the present invention.

FIG. 15A illustrates a cross-sectional side view of a system 500 in accordance with an embodiment of the present invention. The system 500 includes a vial 510, a reservoir 520, a plunger head 522, a plunger arm 524, and a stand 530. The vial 510 includes a septum 512, and the vial allows for containing a fluidic medium. The reservoir 520 has a hollow interior for containing a fluidic medium. The plunger head 522 is located within the reservoir 520 and is moveable within the reservoir 520 to expand or contract an interior volume of the reservoir 520. The plunger head 522 is connected to the plunger arm 524. The reservoir 520 includes a septum 529 at a port of the reservoir 520.

The stand 530 includes a connection structure, such as a transfer guard, or the like, for providing a fluid path from the vial 510 to the reservoir 520. The stand 530 includes a first needle 534, a second needle 532, an air filter 536, a plunger head 540, a pressure providing device 542, and a plunger arm 544 connected to the plunger head 540. The first needle 534 may be used to pierce the septum 512 of the vial 510, and the second needle 532 may be used to pierce the septum 529 of the reservoir 520, and the first needle 534 may be connected to the second needle 532 through the air filter 536. The air filter allows for removing dissolved air from a fluidic medium being transferred from the vial 510 to the reservoir 520.

The plunger head 540, the plunger arm 544, and the pressure providing device 542 allow for assisting with a filling of the reservoir 520. In various embodiments, the pressure providing device 542 comprises a spring, or the like, that is biased toward an expanded position. In various other embodiments, the pressure providing device 542 includes a canister with compressed air, where the compressed air may be released to provide a pressure. An end 546 of the plunger arm 544 of the stand 530 may be inserted into a receptacle 526 of the plunger arm 524, such that a movement of the plunger head 540 causes a movement of the plunger arm 544 that leads to a movement of the plunger arm 524 that causes a movement of the plunger head 522 within the reservoir 520.

Figure 15B:
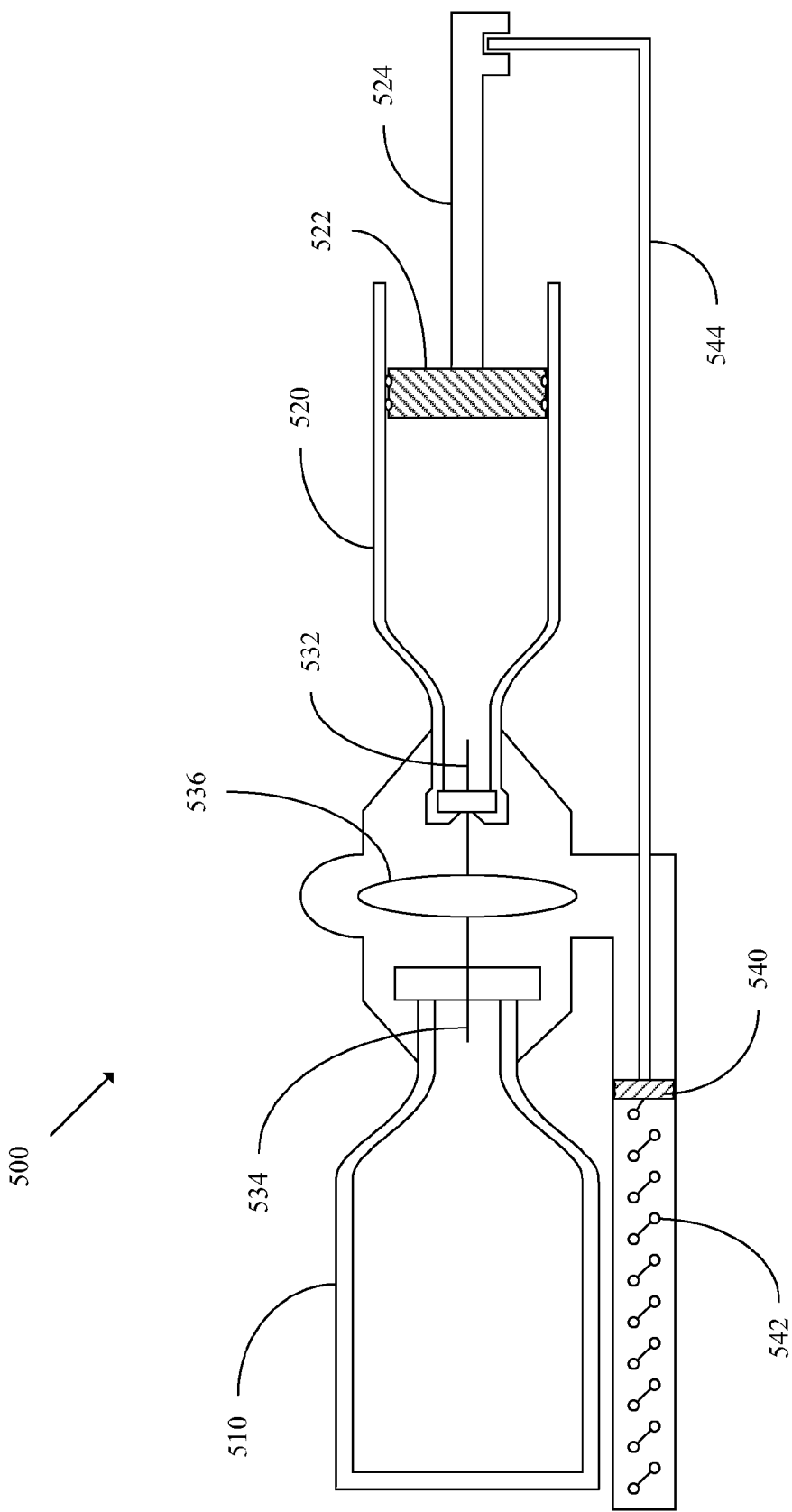
FIG. 15B illustrates a cross-sectional view of a system in accordance with an embodiment of the present invention.

A method in accordance with an embodiment of the present invention allows for using the stand 530 to assist in filling the reservoir 520 from the vial 510. In a first step of the method, the vial 510 and the reservoir 520 are connected to the stand 530. For example, the stand 530 may include a nest for the vial 510 and a nest for the reservoir 520. When the reservoir 520 is attached to the stand 530, the end 546 of the plunger arm 544 of the stand 530 is inserted into the receptacle 526 of the plunger arm 524. In a second step of the method, the pressure providing device 542 is caused to provide a pressure to the plunger head 540 so as to move the plunger head 540 to cause the plunger arm 544 to move, which causes the plunger arm 524 to move and, thus, causes the plunger head 522 to retract within the reservoir 520. FIG. 15B illustrates a cross-sectional side view of the system 500 when the pressure providing device 542 has caused a movement of the plunger head 540 which has caused a movement of the plunger head 522 within the reservoir 520. When the plunger head 522 is retracted within the reservoir 520, a fluidic medium passes from the vial 510 through the air filter 536 and fills into the reservoir 520. The air filter 536 removes dissolved air from the fluidic medium.

Figure 15C:
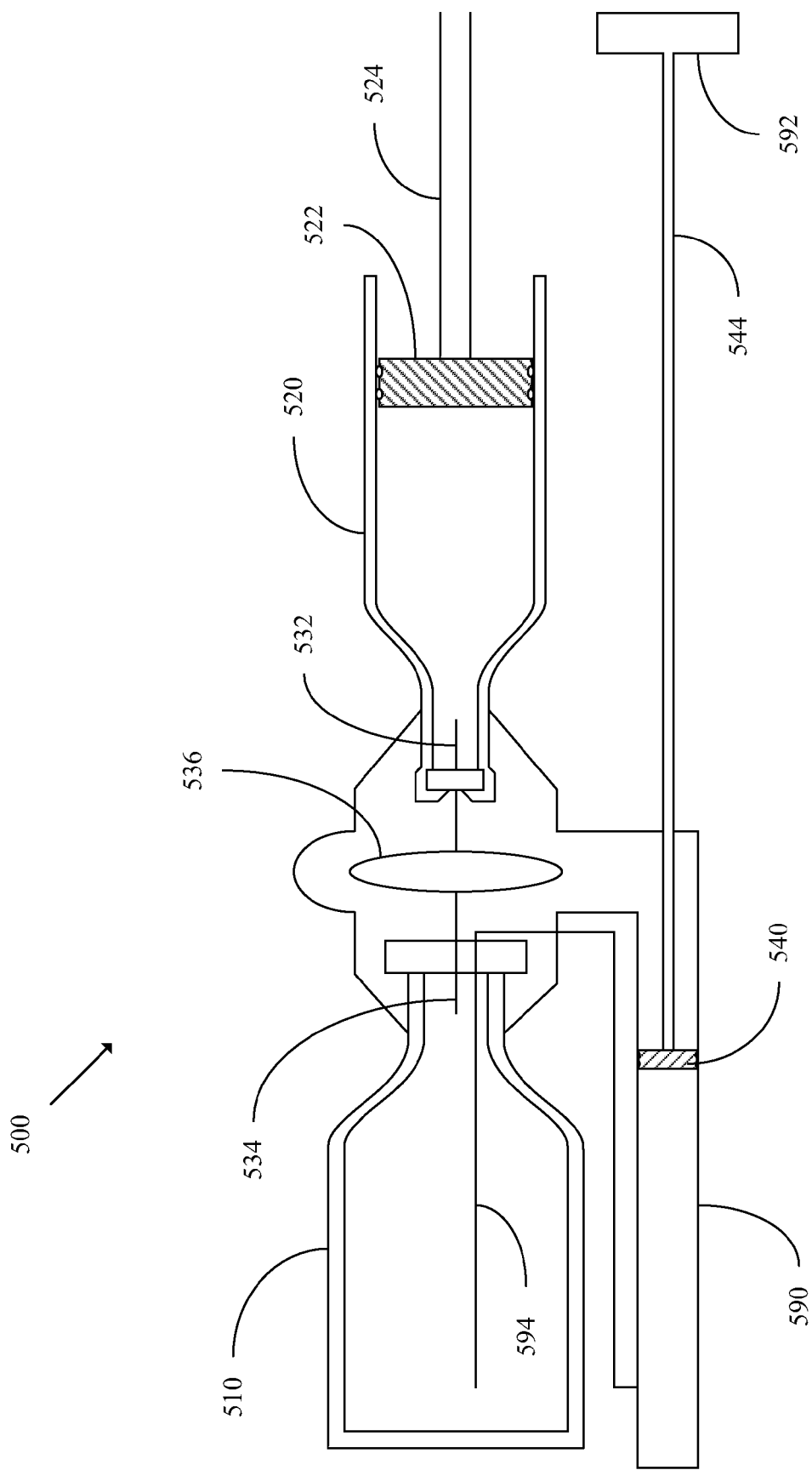
FIG. 15C illustrates a cross-sectional view of a system in accordance with an embodiment of the present invention.

FIG. 15C illustrates a cross-sectional side view of the system 500 in accordance with another embodiment of the present invention. In the embodiment of FIG. 15C, the plunger arm 544 includes a handle 592 at an end of the plunger arm 544. Also, in the embodiment of FIG. 15C, the system 500 includes a pressure channel 590 and an air path member 594. In the embodiment of FIG. 15C, the handle 592 may be pressed to move the plunger head 540 and create a pressure within the pressure channel 590, which then pushes air through the air path member 594 to increase a pressure within the vial 510 and, as a consequence, forces a fluidic medium from the vial 510 to the reservoir 520.

Figure 15D:
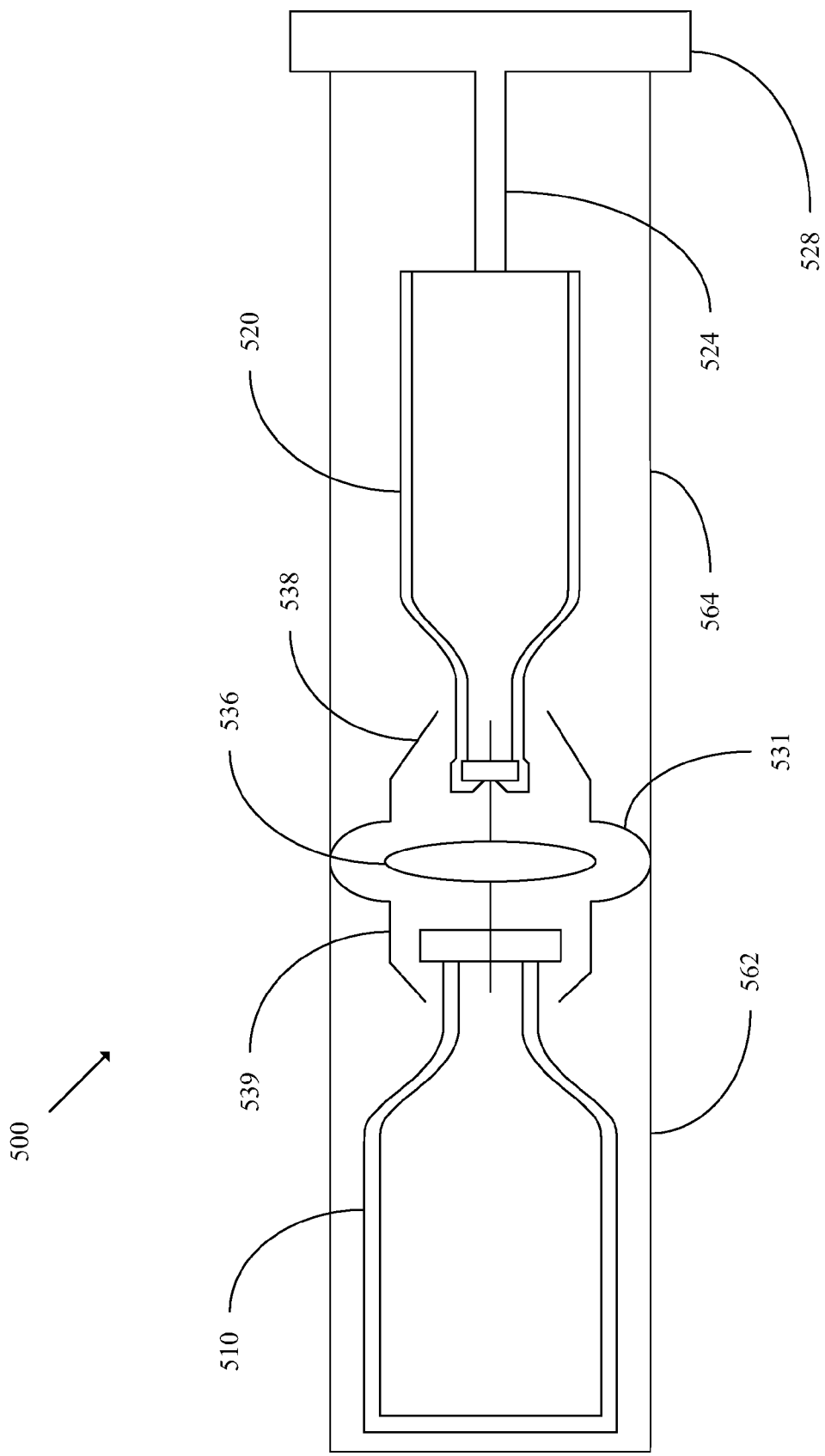
FIG. 15D illustrates a cross-sectional view of a system in accordance with an embodiment of the present invention.
Figure 15E:
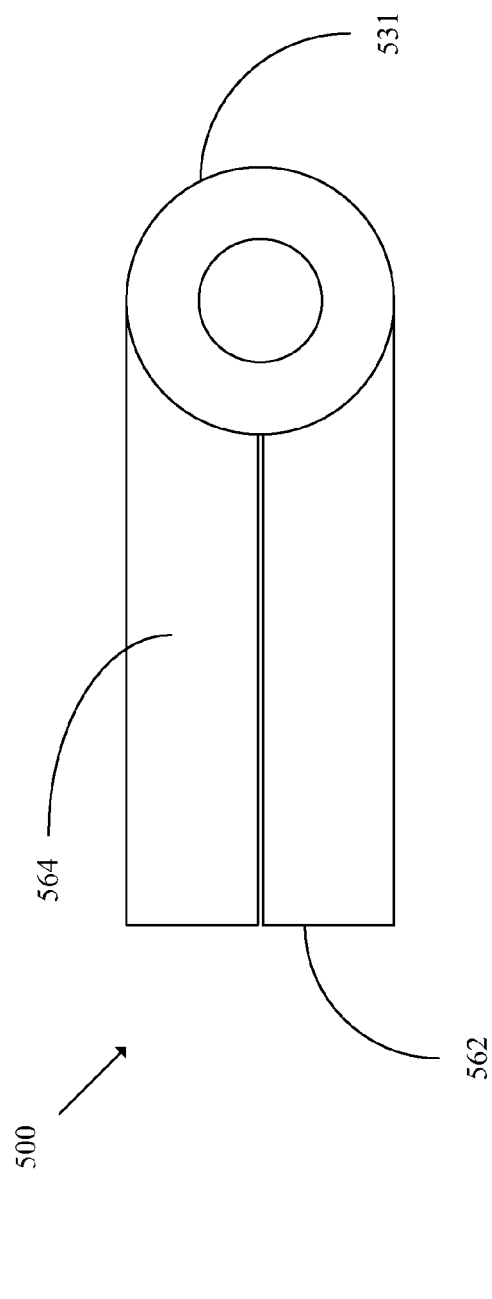
FIG. 15E illustrates a cross-sectional view of a system in accordance with an embodiment of the present invention.
Figure 15F:
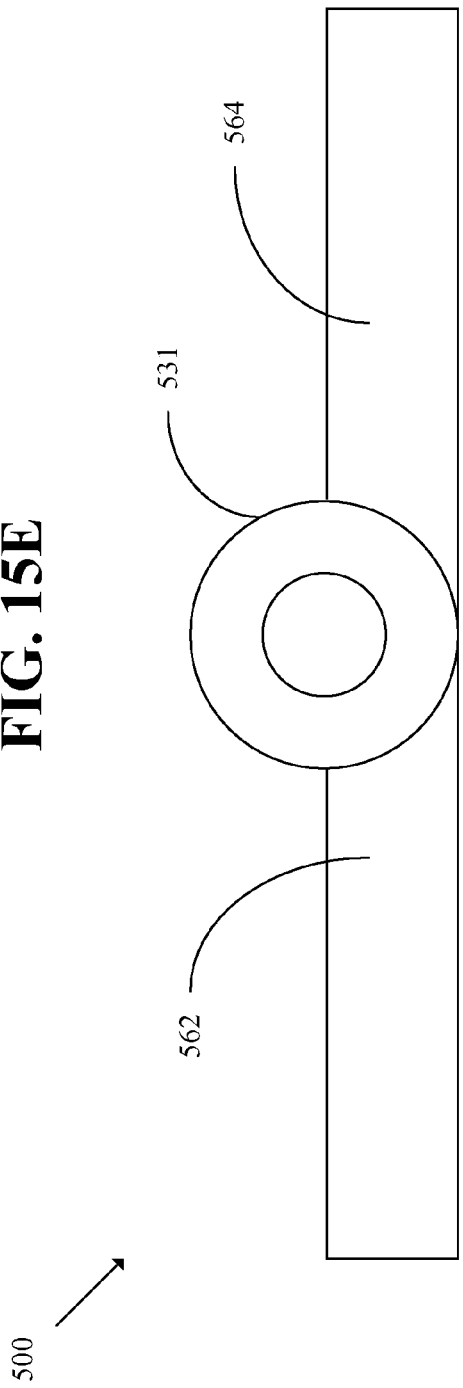
FIG. 15F illustrates a cross-sectional view of a system in accordance with an embodiment of the present invention.

FIG. 15D illustrates a cross-sectional top view of the system 500 in accordance with an embodiment of the present invention. The system 500 includes a first holding member 562 for holding the vial 510, and a second holding member 564 for holding the reservoir 520. A transfer guard 531 that is part of the stand 530 (refer to FIG. 15A) includes a first nest 539 for holding the vial 510 and a second nest 538 for holding the reservoir 520. FIG. 15E illustrates a cross-sectional side view of the system 500 in accordance with an embodiment of the present invention in which the first holding member 562 and the second holding member 564 may be folded together around the transfer guard 531. FIG. 15F illustrates a cross-sectional side view of the system 500 of FIG. 15E in which the first holding member 562 and the second holding member 564 have been unfolded.

Figure 16:
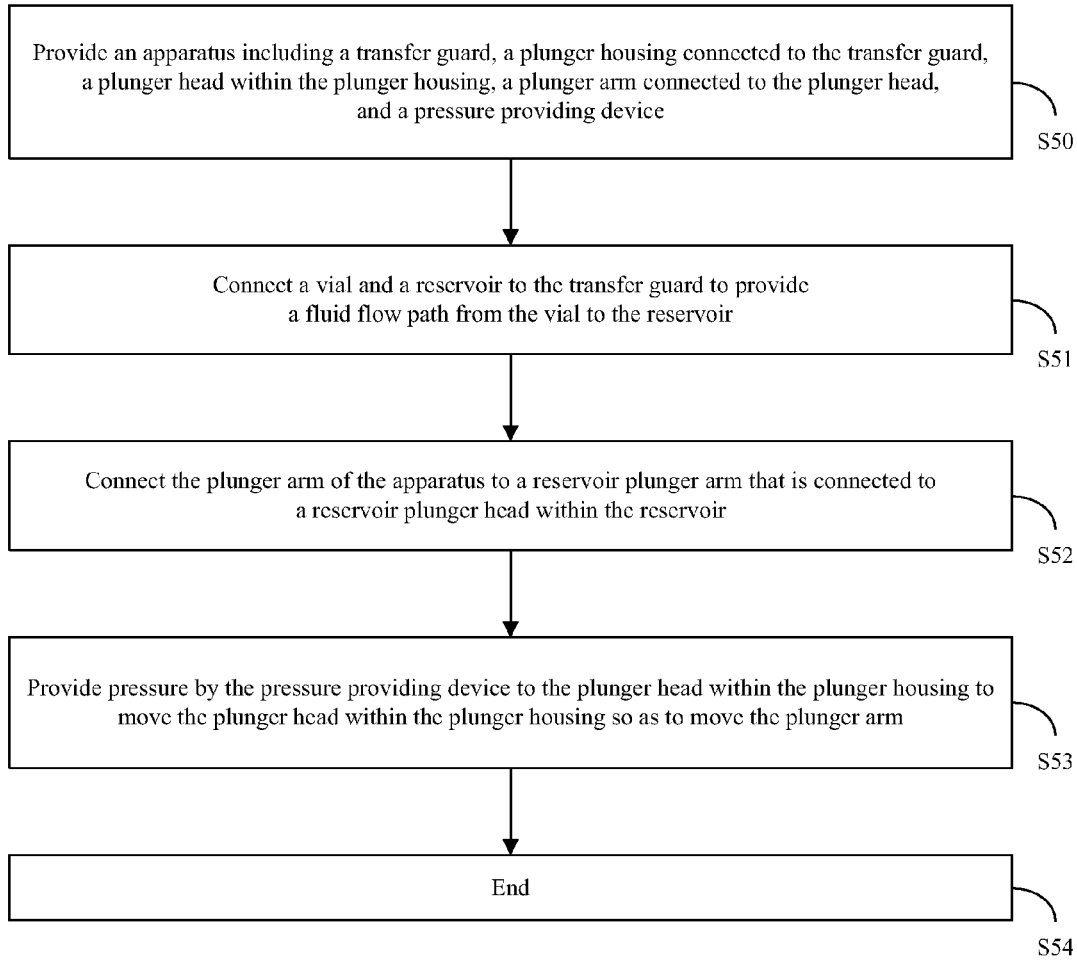
FIG. 16 illustrates a flowchart for a method in accordance with an embodiment of the present invention.

FIG. 16 illustrates a flowchart of a method in accordance with an embodiment of the present invention that allows for filling a reservoir from a vial using an apparatus. In S50, an apparatus is provided that includes a transfer guard, a plunger housing connected to the transfer guard, a plunger head within the plunger housing, a plunger arm connected to the plunger head, and a pressure providing device. The method then continues to S51. In S51, the vial and the reservoir are connected to the transfer guard to provide a fluid flow path from the vial to the reservoir, and the method continues to S52. In S52, the plunger arm of the apparatus is connected to a reservoir plunger arm that is connected to a reservoir plunger head within the reservoir, and the method continues to S53. In S53, pressure is provided by the pressure providing device to the plunger head within the plunger housing to move the plunger head within the plunger housing so as to move the plunger arm. When the plunger arm is connected to the reservoir plunger arm and the plunger arm is moved, the reservoir plunger arm moves so as to move the reservoir plunger head within the reservoir to allow a fluidic medium to flow from the vial to the reservoir through the fluid flow path. The method then ends in S54.

Figure 17:
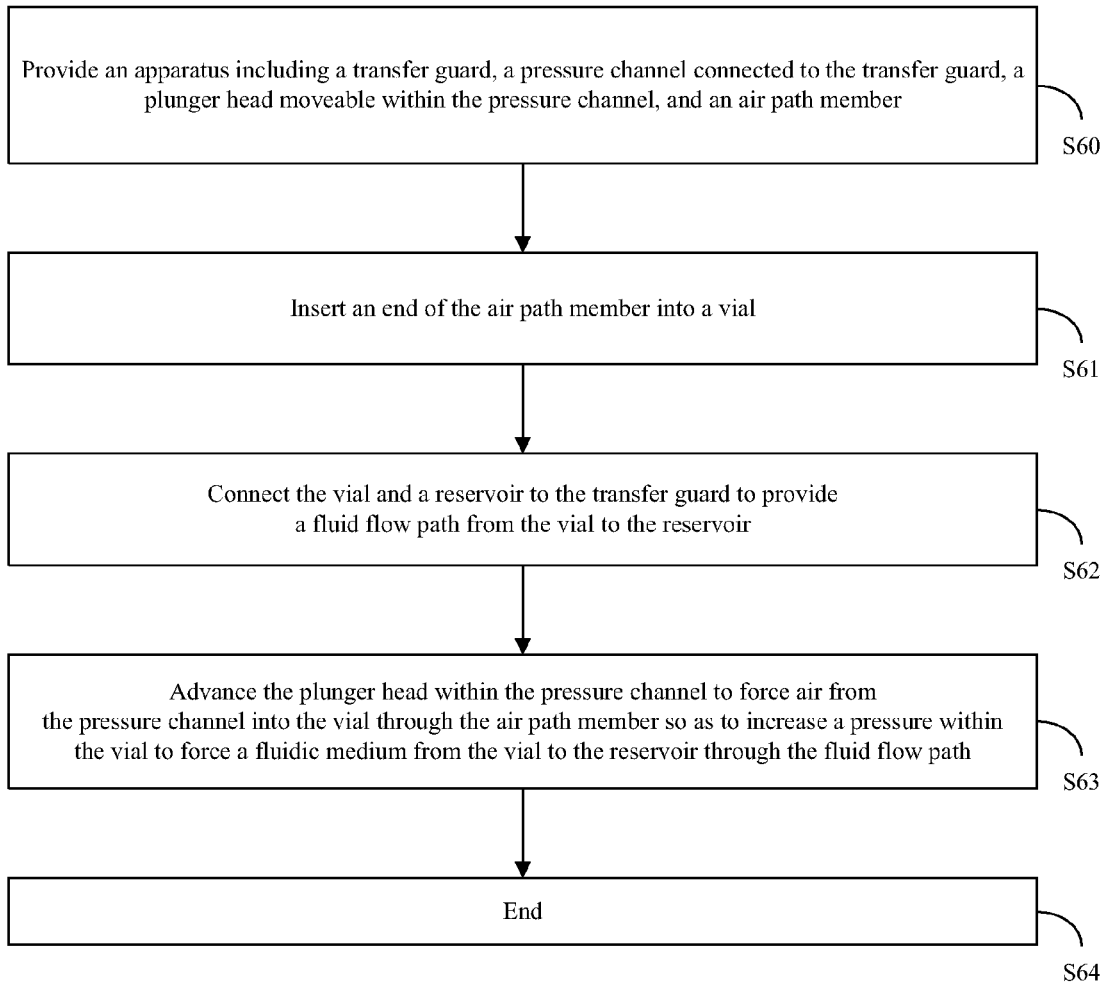
FIG. 17 illustrates a flowchart for a method in accordance with an embodiment of the present invention.

FIG. 17 illustrates a flowchart of a method in accordance with an embodiment of the present invention that allows for filling a reservoir from a vial using an apparatus. In S60, an apparatus is provided that includes a transfer guard, a pressure channel connected to the transfer guard, a plunger head moveable within the pressure channel, and an air path member. The method then continues to S61. In S61, an end of the air path member is inserted into the vial, and the method continues to S62. In S62, the vial and the reservoir are connected to the transfer guard to provide a fluid flow path from the vial to the reservoir, and the method continues to S63. In S63, the plunger head is advanced within the pressure channel to force air from the pressure channel into the vial through the air path member so as to increase a pressure within the vial to force a fluidic medium from the vial to the reservoir through the fluid flow path. The method then ends in S64.

Figure 18A:
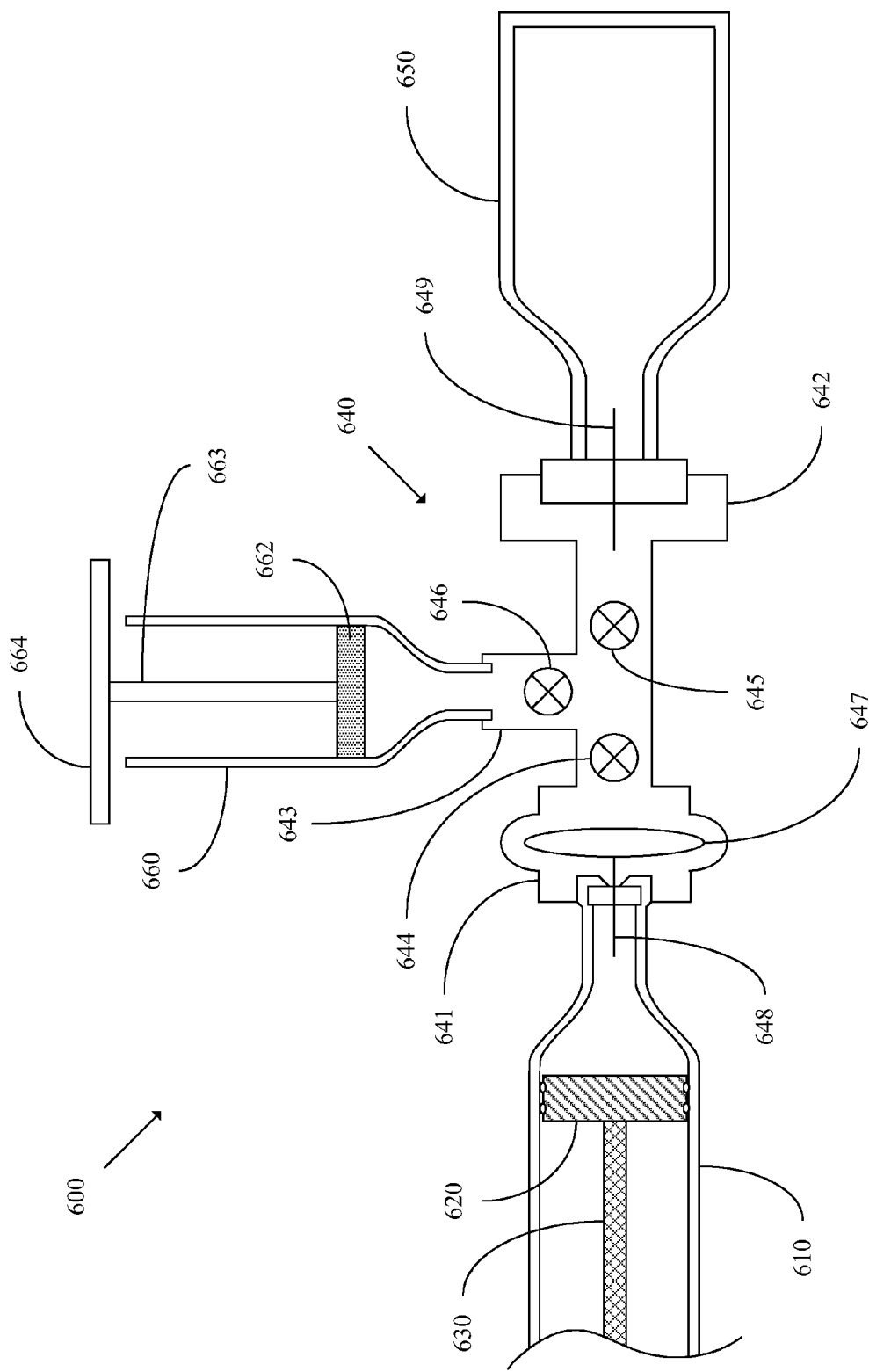
FIG. 18A illustrates a cross-sectional view of a system in accordance with an embodiment of the present invention.

FIG. 18A illustrates a cross-sectional view of a system 600 in accordance with an embodiment of the present invention. The system 600 includes a reservoir 610, a plunger head 620, a plunger arm 630, a transfer guard 640, a vial 650, and a vacuum plunger 660. The vial 650 has a hollow interior for containing a fluidic medium. The reservoir 610 has a hollow interior for containing a fluidic medium. The plunger head 620 is located within the reservoir 610 and is moveable within the reservoir 610 to expand or contract an interior volume of the reservoir 610. The plunger head 620 is connected to the plunger arm 630. The vacuum plunger 660 includes a plunger head 662, a plunger arm 663 connected to the plunger head 662, and a handle 664 connected to the plunger arm 663. The plunger head 662 is moveable within a housing of the vacuum plunger 660 to expand or contract an interior volume of the vacuum plunger 660.

The transfer guard 640 includes a reservoir nest 641, a vial nest 642, a vacuum plunger nest 643, a first valve 644, a second valve 645, a third valve 646, a filter 647, a first needle 648, and a second needle 649. The reservoir nest 641 is configured to be connected to the reservoir 610, such that the first needle 648 is inserted into the interior volume of the reservoir 610. The vial nest 642 is configured to be connected to the vial 650, such that the second needle 649 is inserted into an interior volume of the vial 650. The vacuum plunger nest 643 is configured to be connected to the vacuum plunger 660. The first valve 644 allows for a fluidic medium to flow into the reservoir 610 when the first valve 644 is open, and prevents a fluidic medium from flowing into the reservoir 610 when the first valve 644 is closed. The second valve 645 allows for a fluidic medium to flow out of the vial 650 when the second valve 645 is open, and prevents a fluidic medium from flowing out of the vial 650 when the second valve 645 is closed. The third valve 646 allows for a fluidic medium to flow into and out of the vacuum plunger 660 when the third valve 646 is open, and prevents a fluidic medium from flowing into or out of the vacuum plunger 660 when the third valve 646 is closed. The filter 647 allows for filtering air from a fluidic medium.

A method in accordance with the present invention allows for filling the reservoir 610 using the transfer guard 640. In a step of the method, the reservoir nest 641 is connected to the reservoir 610, the vial nest 642 is connected to the vial 650, and the vacuum plunger nest 643 is connected to the vacuum plunger 660. Also, in an initial position, the plunger head 662 is depressed within the vacuum plunger 660, and the plunger head 620 is depressed within the reservoir 610. Moreover, in an initial state, the first valve 644, the second valve 645, and the third valve 646 are all closed. An example of the system 600 in such a state is illustrated in FIG. 18A.

Figure 18B:
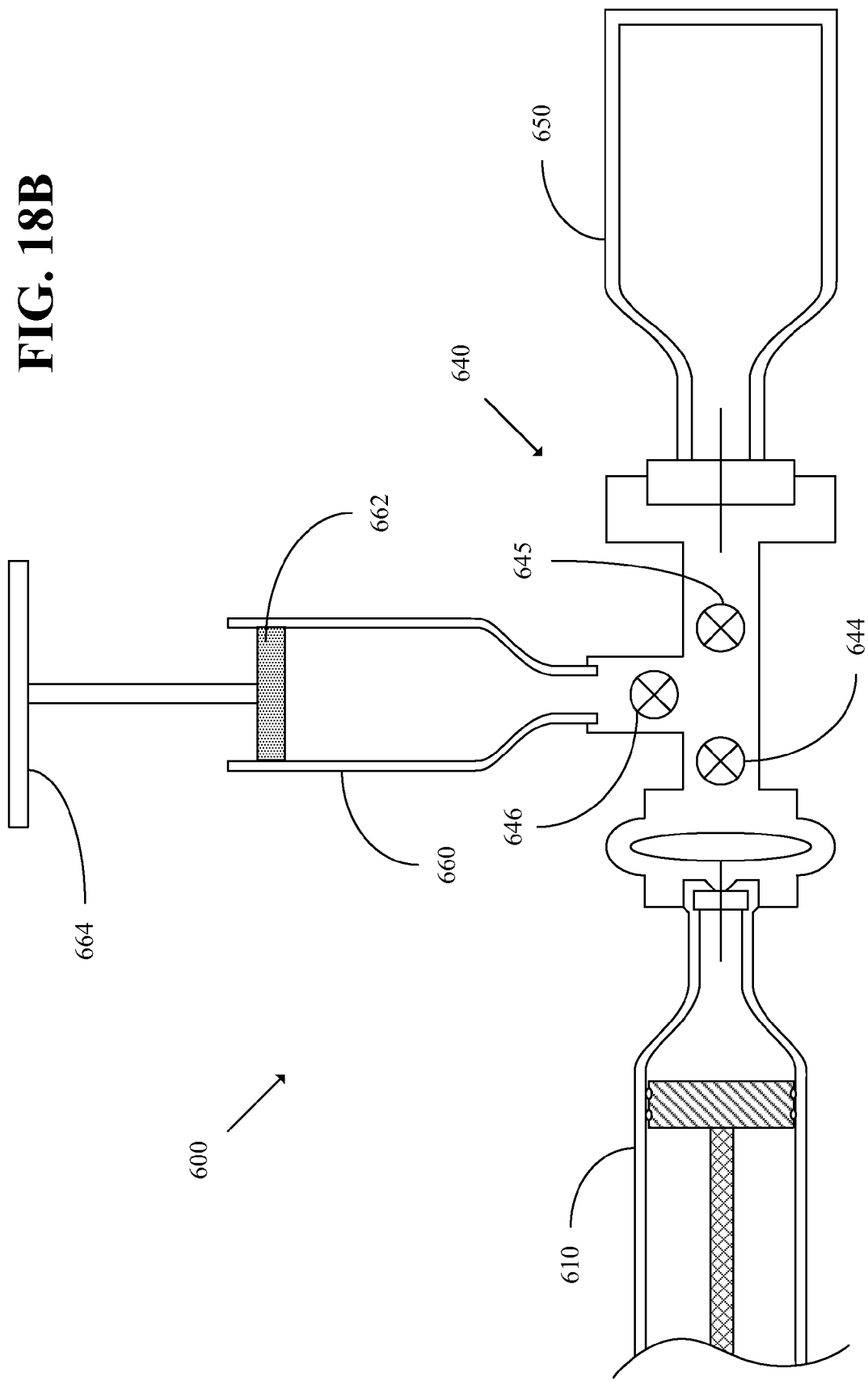
FIG. 18B illustrates a cross-sectional view of a system in accordance with an embodiment of the present invention.

In another step of the method, the second valve 645 and the third valve 646 are opened, and the handle 664 is pulled to cause the plunger head 662 to retract within a housing of the vacuum plunger 660. FIG. 18B illustrates a cross-sectional view of the system 600 in accordance with an embodiment of the present invention when the plunger head 662 has been retracted within a housing of the vacuum plunger 660. By retracting the plunger head 662 within the housing of the vacuum plunger 660 when the second valve 645 and the third valve 646 are open, a fluidic medium is caused to flow from the vial 650 into an interior volume of the vacuum plunger 660.

Figure 18C:
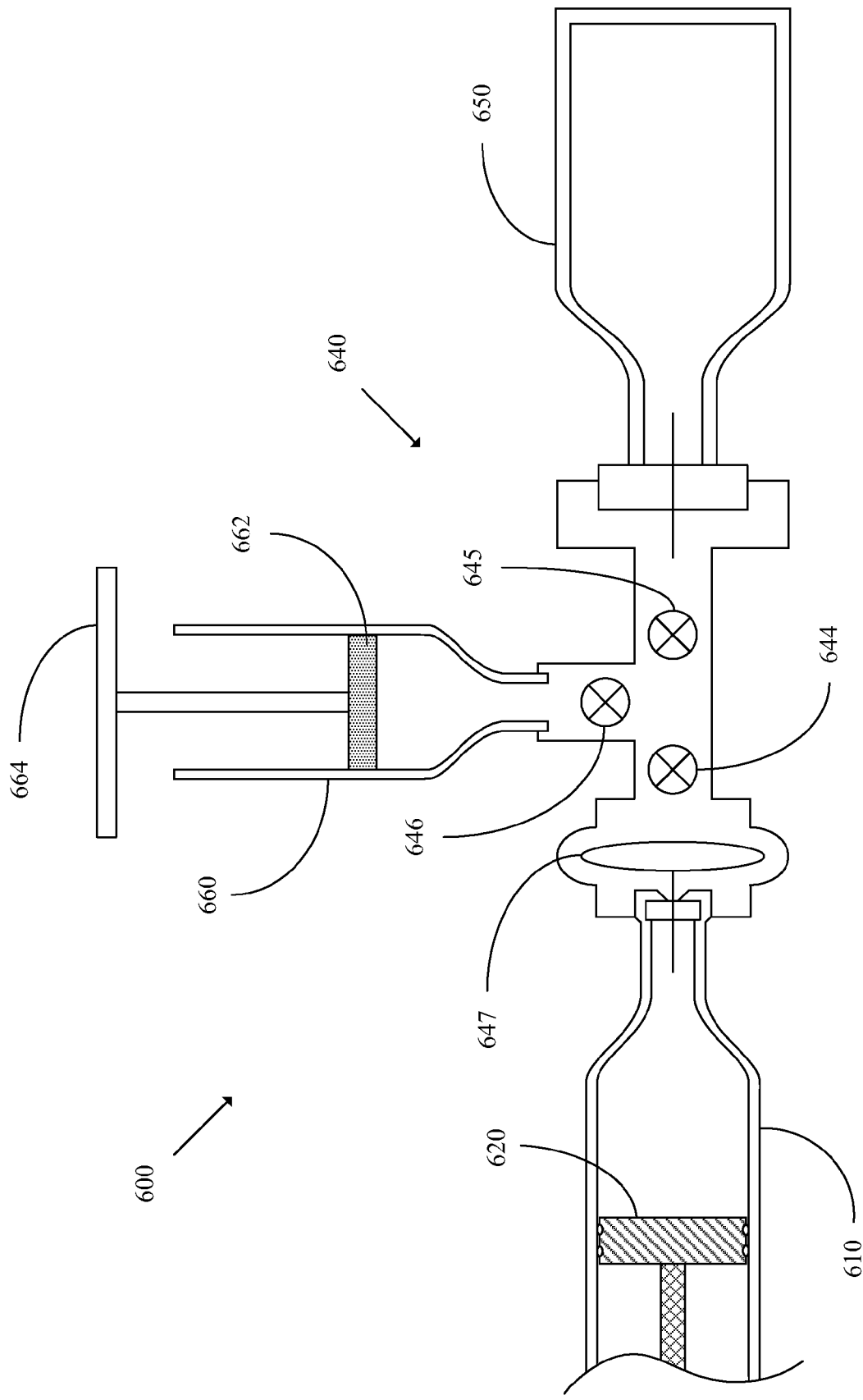
FIG. 18C illustrates a cross-sectional view of a system in accordance with an embodiment of the present invention.

In yet another step of the method, the second valve 645 is closed and the first valve 644 is opened, and the handle 664 is pushed to cause the plunger head 662 to advance within the housing of the vacuum plunger 660. FIG. 18C illustrates a cross-sectional view of the system 600 in accordance with an embodiment of the present invention when the plunger head 662 has been advanced within the housing of the vacuum plunger 660. By advancing the plunger head 662 within the housing of the vacuum plunger 660 when the third valve 646 and the first valve 644 are open, a fluidic medium is caused to flow from the vacuum plunger 660 into the interior volume of the reservoir 610 while forcing the plunger head 620 to retract within the reservoir 610. The filter 647 filters air bubbles out of the fluidic medium as the fluidic medium passes from the vacuum plunger 660 to the reservoir 610.

Therefore, embodiments of the present invention allow for incorporating a series of valves into a transfer guard and for using a hand operated vacuum plunger and a filter or membrane to filter out air bubbles. Moreover, embodiments of the present invention allow for a two step degassing process in which a first step involves vacuum aspiration and a second step involves pushing a fluidic medium across a filter. Thus, embodiments of the present invention allow for filling a reservoir by pushing a fluidic medium across a filter and into the reservoir. In some embodiments, cavitation is used to degas a fluidic medium.

Figure 19:
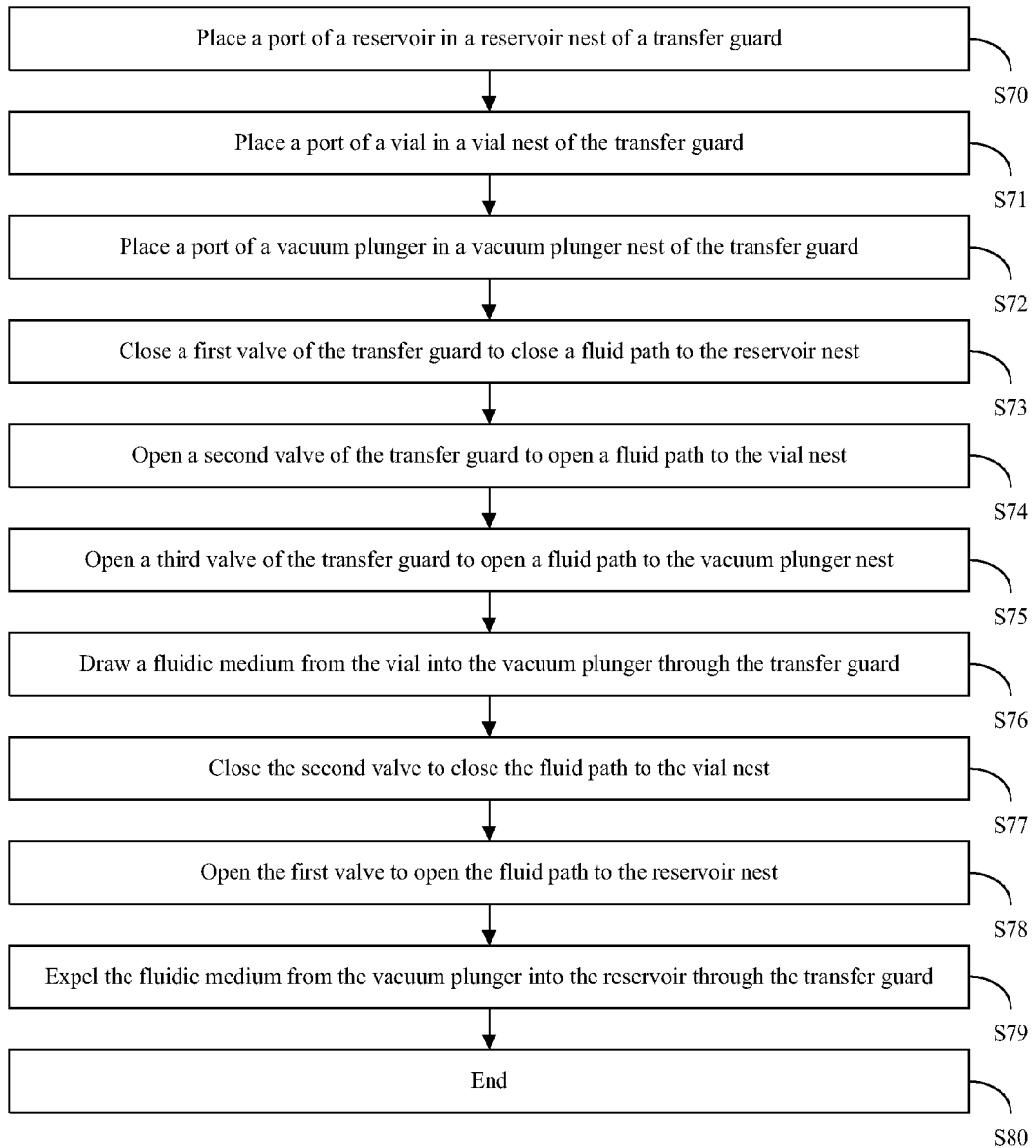
FIG. 19 illustrates a flowchart for a method in accordance with an embodiment of the present invention.

FIG. 19 illustrates a flowchart of a method in accordance with an embodiment of the present invention. In S70, a port of a reservoir is placed in a reservoir nest of a transfer guard, and the method continues to S71. In S71, a port of a vial is placed in a vial nest of the transfer guard, and the method continues to S72. In S72, a port of a vacuum plunger is placed in a vacuum plunger nest of the transfer guard, and the method continues to S73. In S73, a first valve of the transfer guard is closed to close a fluid path to the reservoir nest, and the method continues to S74. In S74, a second valve of the transfer guard is opened to open a fluid path to the vial nest, and the method continues to S75. In S75, a third valve of the transfer guard is opened to open a fluid path to the vacuum plunger nest, and the method continues to S76. In S76, a fluidic medium is drawn from the vial into the vacuum plunger through the transfer guard, and the method continues to S77. In S77, the second valve is closed to close the fluid path to the vial nest, and the method continues to S78. In S78, the first valve is opened to open the fluid path to the reservoir nest, and the method continues to S79. In S79, the fluidic medium is expelled from the vacuum plunger into the reservoir through the transfer guard, and then the method ends in S80.

Figure 20:
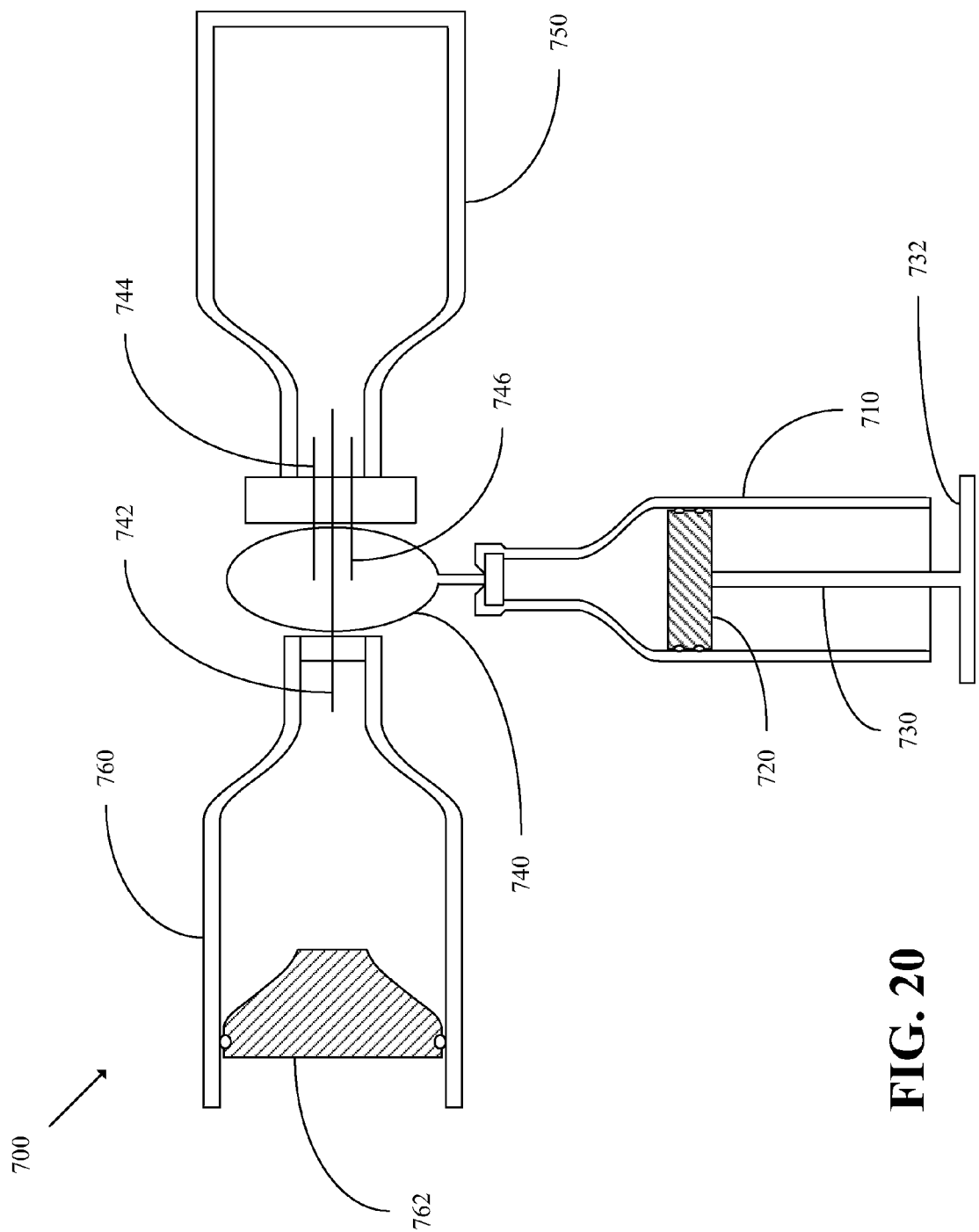
FIG. 20 illustrates a cross-sectional view of a system in accordance with an embodiment of the present invention.

FIG. 20 illustrates a cross-sectional view of a system 700 in accordance with an embodiment of the present invention. The system 700 includes a reservoir 710, a plunger head 720, a plunger arm 730, a handle 732, a vial 750, a pressure source 760, a piston 762, an air needle 742, a first fluid needle 744, a second fluid needle 746, and a filter 740. The piston 762 is moveable within the pressure source 760 to generate pressure. The air needle 742 provides a path for air to pass from the pressure source 760 to an interior of the vial 750. The vial 750 contains a fluidic medium. The vial 750 is connected to the filter 740 by the first fluid needle 744 and the second fluid needle 746. The filter is connected to a port of the reservoir 710. The reservoir 710 has an interior volume for holding a fluidic medium. The plunger head 720 is able to slide within the reservoir 710.

During a filling operation with the system 700, the piston 762 is advanced within the pressure source 760 to force air through the air needle 742 and into the vial 750. The increased pressure in the vial 750 due to the pressure from the pressure source 760 causes a fluidic medium in the vial 750 to be expelled through the first fluid needle 744 and the second fluid needle 746 to the filter 740. The filter 740 filters air bubbles out of the fluidic medium, and then the fluidic medium fills into the interior volume of the reservoir 710. Thus, in various embodiments, a fluidic medium or solution, such as insulin, is forced across a filter during filling, and the fluidic medium is pushed into a reservoir rather than being pulled into the reservoir. Also, while the system 700 is illustrated as a multiple needle design with a first fluid needle 744 and a second fluid needle 746, it should be appreciated that, in various embodiments, more than two fluid needles may be used between the vial 750 and the filter 740 and that, in various other embodiments, a single fluid needle may be used between the vial 750 and the filter 740.

Figure 21:
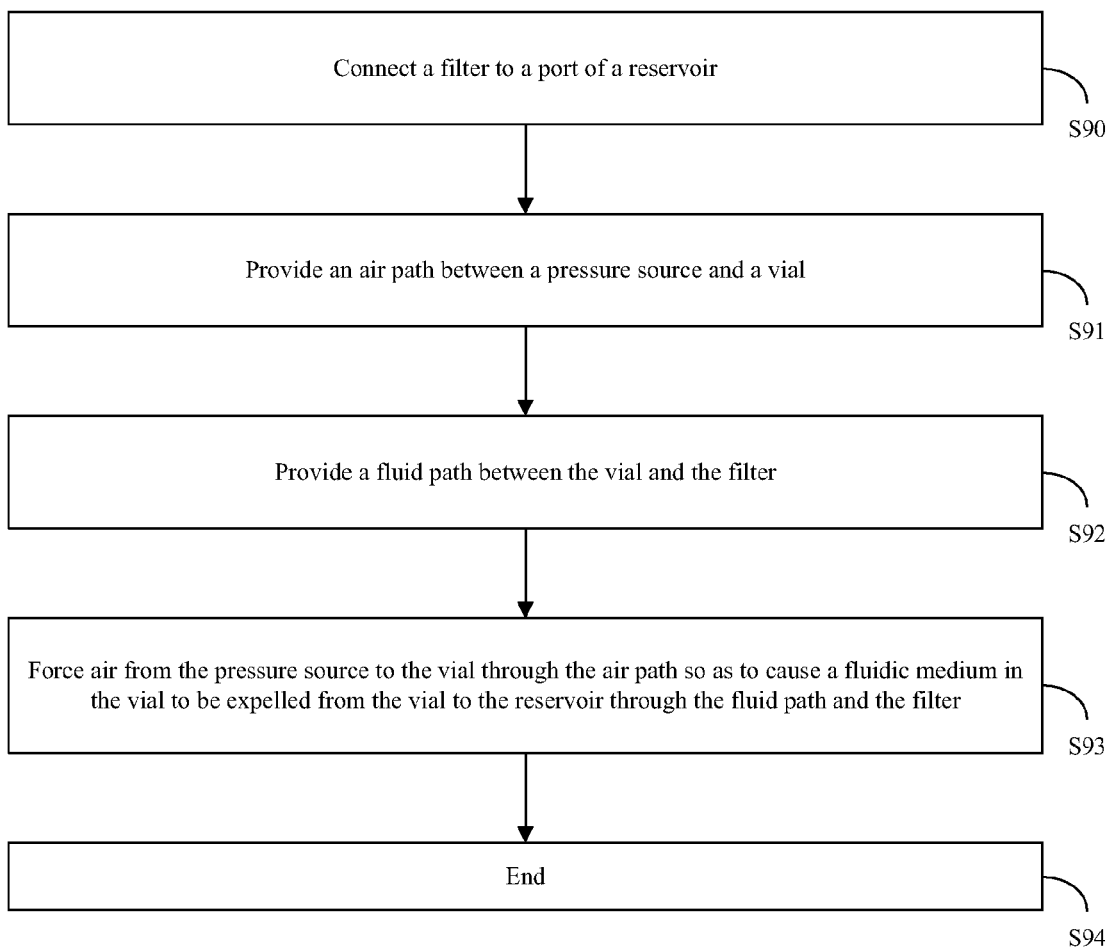
FIG. 21 illustrates a flowchart for a method in accordance with an embodiment of the present invention.

FIG. 21 illustrates a flowchart of a method in accordance with an embodiment of the present invention. In S90, a filter is connected to a port of a reservoir, and the method continues to S91. In S91, an air path is provided between a pressure source and a vial, and the method continues to S92. In S92, a fluid path is provided between the vial and the filter, and the method continues to S93. In S93, air is forced from the pressure source to the vial through the air path so as to cause a fluidic medium in the vial to be expelled from the vial to the reservoir through the fluid path and the filter. The method then ends in S94.

Figure 22:
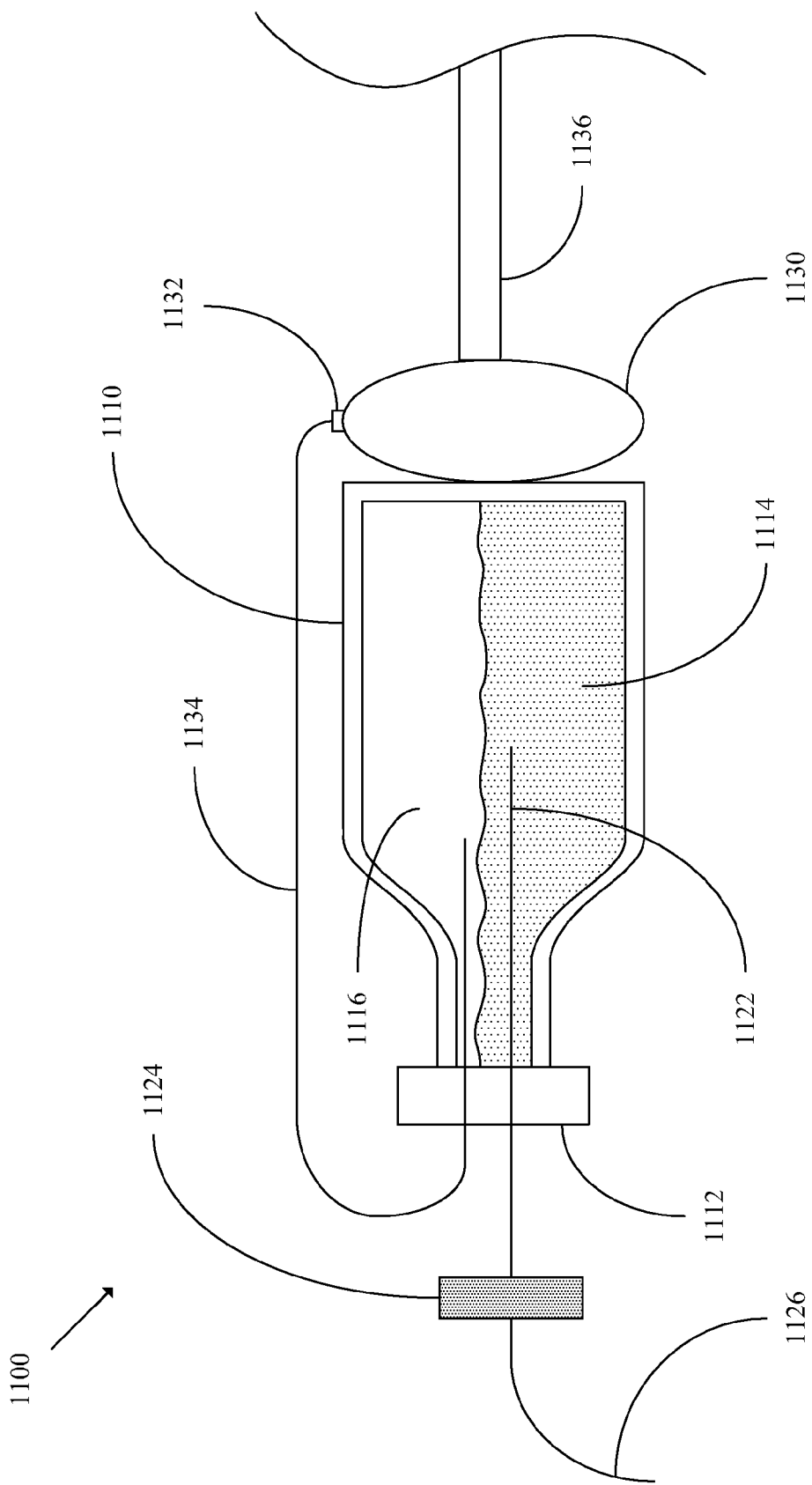
FIG. 22 illustrates a cross-sectional view of a system in accordance with an embodiment of the present invention.

FIG. 22 illustrates a cross-sectional view of a system 1100 in accordance with an embodiment of the present invention. The system 1100 includes a vial 1110, an air sack 1130, a one-way valve 1132, an air line 1134, a drive shaft 1136, a fluid line 1122, a filter 1124, and an insertion line 1126. The vial 1110 contains a fluidic medium 1114 within a housing of the vial 1110. An air space is provided in the vial 1110 in an area 1116 above the fluidic medium 1114. The fluid line 1122 may be inserted into the vial 1110 through a septum 1112 of the vial 1110. One end of the air line 1134 is connected to the one-way valve 1132, and another end of the air line 1134 is inserted into the area 1116 of the vial 1110 above the fluidic medium 1114. The one-way valve 1132 allows for air to be pushed out of the air sack 1130 and through the air line 1134 into the area 1116 in the vial 1110.

The drive shaft 1136 allows for compressing the air sack 1130 so as to cause air to be pushed through the one-way valve 1132 and through the air line 1134. One end of the fluid line 1122 is positioned within the fluidic medium 1114 in the vial 1110, and another end of the fluid line 1122 is connected to the filter 1124. The filter 1124 allows for filtering air bubbles out of a fluidic medium that passes from the fluid line 1122 to the insertion line 1126 through the filter 1124. During operation, the drive shaft 1136 compresses the bulb or air sack 1130 to force air into the vial 1110 through the air line 1134. The air that exits the air line 1134 in the vial 1110 is provided into the area 1116 that is above the fluidic medium 1114, so the air from the air line 1134 is provided into the vial 1110 without percolating through the fluidic medium 1114. An increase in pressure caused by air from the air line 1134 forces the fluidic medium 1114 through the fluid line 1122 to the filter 1124 and on to the insertion line 1126. In various embodiments, the insertion line 1126 is inserted into a reservoir (not shown in FIG. 22), such that the reservoir is able to be filled from the vial 1110. Also, in various alternate embodiments, the fluidic medium 1114 may be delivered directly through the fluid line 1122 without passing through the filter 1124.

Figure 23:
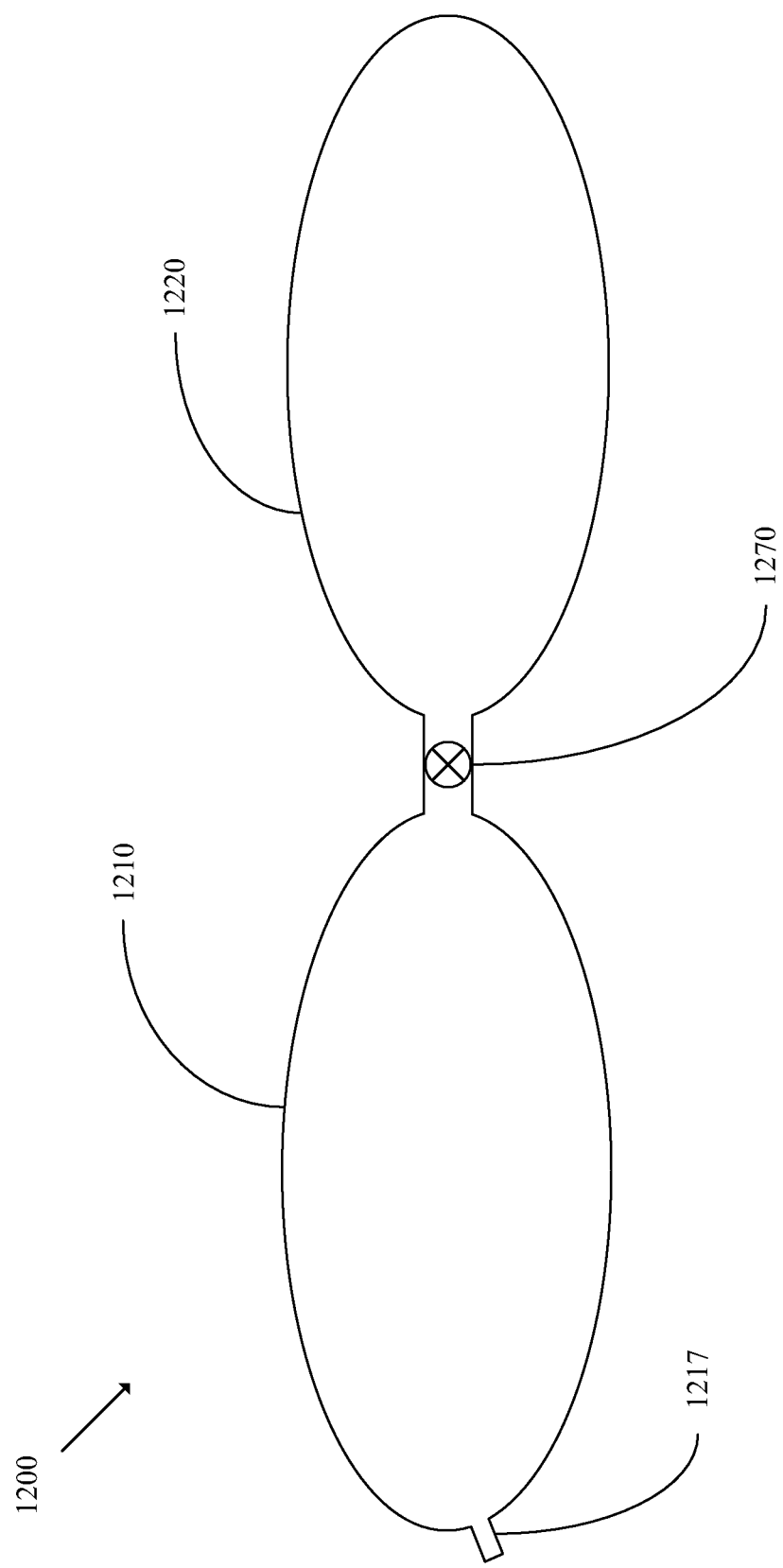
FIG. 23 illustrates a system in accordance with an embodiment of the present invention.

FIG. 23 illustrates a system 1200 in accordance with an embodiment of the present invention. The system 1200 includes a pressure sack 1220, a one-way valve 1270, a reservoir sack 1210, and an outlet path 1217. The system 1200 is configured such that when the reservoir sack 1210 contains a fluidic medium, the pressure sack 1220 may be used to force air through the one-way valve 1270 and, thus, cause the fluidic medium to be expelled from the reservoir sack 1210 through the outlet path 1217.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. Various modifications and changes that come within the meaning and range of equivalency of the claims are intended to be within the scope of the invention.

What is claimed is:

1. A system for use in filling one or more reservoirs, the system comprising:
   a vial having an interior volume for containing a liquid;
   a diaphragm arranged in the vial, the diaphragm defining a pressurizable volume, the diaphragm separating the interior volume of the vial from the pressurizable volume, the diaphragm inflatable to expel liquid from the interior volume in a case where a pressure within the pressurizable volume is increased to inflate the diaphragm; and
   a reservoir having an interior volume;
   said diaphragm being inflatable to force liquid out of the interior volume of the vial and into the interior volume of the reservoir in a case where the interior volume of the vial is holding the liquid and the interior volume of the vial is connected to the interior volume of the reservoir by a needle and the pressure within the pressurizable volume is increased;
   wherein a flow path between the interior volume of the vial and the interior volume of the reservoir is configured to reduce air bubbles from passing in the liquid as the liquid is transferred from the interior volume of the vial to the interior volume of the reservoir.

2. The system of claim 1,
   said diaphragm deflatable to increase the interior volume of the vial in a case where the pressure within the pressurizable volume is decreased.

3. The system of claim 1,
   said diaphragm attached to an inner surface of the vial.

4. The system of claim 1, further comprising:
   a pressure providing device for changing a pressure within the pressurizable volume.

5. The system of claim 4,
   said pressure providing device including a syringe;
   said syringe connectable to the vial such that in a case where the syringe is filled with air and is connected to the vial and a plunger head within the syringe is advanced, a pressure within the pressurizable volume is increased so as to cause the diaphragm to inflate and reduce the interior volume of the vial.

6. The system of claim 1, further comprising:
   a reservoir having an interior volume;
   said diaphragm deflatable to evacuate air from the interior volume of the reservoir into the interior volume of the vial in a case where the interior volume of the reservoir and the interior volume of the vial are connected by a needle and a vacuum is applied to the pressurizable volume of the vial.

7. The system of claim 1, said vial further comprising:
a first port for allowing liquid to be expelled from the interior volume of the vial; and
a second port for allowing a gas to be injected into the pressurizable volume of the vial.

8. A method for filling a reservoir, comprising:
providing a fluid flow path between an interior volume of a vial and an interior volume of the reservoir;
applying a pressure to a pressurizable volume of the vial so as to inflate a diaphragm to cause liquid to be expelled from the interior volume of the vial into the interior volume of the reservoir; and
filtering air from liquid as the liquid is expelled from the interior volume of the vial to the interior volume of the reservoir.

9. The method of claim 8, said applying the pressure comprising:
injecting at least one of a gas and a liquid from a pressure providing device into the pressurizable volume of the vial.

10. The method of claim 9,
said pressure providing device including a syringe;
said injecting comprising injecting the at least one of the gas and the liquid from the syringe into the pressurizable volume of the vial by advancing a plunger head within the syringe.

11. The method of claim 8, further comprising:
applying a vacuum to the pressurizable volume of the vial so as to deflate the diaphragm to cause air to be evacuated from the interior volume of the reservoir into the interior volume of the vial.

12. The method of claim 11,
said applying the vacuum occurring before said applying the pressure.

13. The system of claim 1, further comprising:
a filter arranged in the flow path to filter air bubbles so as to reduce air bubbles from passing in the liquid as the liquid is transferred from the interior volume of the vial to the interior volume of the reservoir.

14. The system of claim 4,
wherein the pressure providing device is in communication with the pressurizable volume; and
wherein the pressure providing device is external the vial.

* * * * *